(12) United States Patent
Grunenberg et al.

(10) Patent No.: US 8,877,933 B2
(45) Date of Patent: Nov. 4, 2014

(54) THERMODYNAMICALLY STABLE FORM OF A TOSYLATE SALT

(75) Inventors: Alfons Grunenberg, Dormagen (DE); Jana Lenz, Wuppertal (DE)

(73) Assignee: Bayer Intellectual Property GmbH, Monheim (DE)

( * ) Notice: Subject to any disclaimer, the term of this patent is extended or adjusted under 35 U.S.C. 154(b) by 825 days.

(21) Appl. No.: 11/664,363

(22) PCT Filed: Sep. 20, 2005

(86) PCT No.: PCT/EP2005/010119
§ 371 (c)(1),
(2), (4) Date: Jun. 20, 2008

(87) PCT Pub. No.: WO2006/034797
PCT Pub. Date: Apr. 6, 2006

(65) Prior Publication Data
US 2009/0215833 A1    Aug. 27, 2009

(30) Foreign Application Priority Data
Sep. 29, 2004  (EP) .................................... 04023130

(51) Int. Cl.
*A61K 31/44* (2006.01)
*A61P 35/00* (2006.01)
*C07D 213/81* (2006.01)

(52) U.S. Cl.
CPC .................. *C07D 213/81* (2013.01)
USPC ....................................................... 546/291

(58) Field of Classification Search
USPC ....................................................... 546/291
See application file for complete search history.

(56) References Cited

U.S. PATENT DOCUMENTS

| | | | |
|---|---|---|---|
| 5,629,425 A | 5/1997 | LaBell et al. |
| 6,140,321 A | 10/2000 | Imai et al. |
| 6,187,799 B1 | 2/2001 | Wood et al. |
| 6,344,476 B1 | 2/2002 | Ranges et al. |
| 7,235,576 B1 | 6/2007 | Riedl et al. |
| 7,329,670 B1 | 2/2008 | Dumas et al. |
| 7,351,834 B1 | 4/2008 | Riedl et al. |
| 7,371,763 B2 | 5/2008 | Dumas |
| 7,517,880 B2 | 4/2009 | Miller et al. |
| 7,528,255 B2 | 5/2009 | Riedl et al. |
| 7,557,129 B2 | 7/2009 | Scott et al. |
| 7,625,915 B2 | 12/2009 | Dumas et al. |
| 7,678,811 B2 | 3/2010 | Dumas et al. |
| 7,838,524 B2 | 11/2010 | Lee et al. |
| 7,838,541 B2 | 11/2010 | Dumas et al. |
| 7,897,623 B2 | 3/2011 | Riedl et al. |
| 7,928,227 B2 | 4/2011 | Boyer et al. |
| 7,928,239 B2 | 4/2011 | Dumas et al. |
| 8,071,616 B2 | 12/2011 | Dumas et al. |
| 8,076,488 B2 | 12/2011 | Dumas et al. |
| 8,101,773 B2 | 1/2012 | Smith et al. |
| 8,110,587 B2 | 2/2012 | Dumas et al. |
| 8,124,630 B2 | 2/2012 | Riedl et al. |
| 8,124,782 B2 | 2/2012 | Logers, et al. |
| 8,207,166 B2 | 6/2012 | Lee et al. |
| 8,217,061 B2 | 7/2012 | Gavenda et al. |
| 8,242,147 B2 | 8/2012 | Dumas |
| 8,329,408 B2 | 12/2012 | Wilhelm |
| 8,618,141 B2 | 12/2013 | Dumas |
| 8,637,553 B2 | 1/2014 | Boyer et al. |
| 2003/0144278 A1 | 7/2003 | Riedl et al. |
| 2003/0181442 A1 | 9/2003 | Riedl et al. |
| 2003/0207872 A1 | 11/2003 | Riedl et al. |
| 2005/0048533 A1* | 3/2005 | Sidransky et al. ................ 435/6 |
| 2005/0059703 A1 | 3/2005 | Wilhelm et al. |
| 2006/0034797 A1 | 2/2006 | Arien et al. |
| 2006/0058358 A1 | 3/2006 | Dumas et al. |
| 2007/0020704 A1 | 1/2007 | Wilhelm et al. |
| 2008/0153823 A1 | 6/2008 | Riedl et al. |
| 2008/0227828 A1 | 9/2008 | Dumas et al. |
| 2008/0242707 A1 | 10/2008 | Schuckler et al. |
| 2009/0215835 A1 | 8/2009 | Wilhelm |
| 2010/0035888 A1 | 2/2010 | Sandner |
| 2010/0063112 A1 | 3/2010 | Grunenberg et al. |
| 2010/0113533 A1 | 5/2010 | Stiehl et al. |
| 2010/0144749 A1 | 6/2010 | Wilhelm |
| 2010/0173953 A1 | 7/2010 | Grunenberg et al. |
| 2010/0173954 A1 | 7/2010 | Wilhelm et al. |
| 2010/0267777 A1 | 10/2010 | Wilhelm et al. |

(Continued)

FOREIGN PATENT DOCUMENTS

CL      2543-05       4/2006
EP    1 450 799 B9    9/2004

(Continued)

OTHER PUBLICATIONS

Hotte, et al., "BAY 43/9006: Early Clinical Data in Patients with Advanced Solid Malignancies", Cur. Pharma. Design, 8.25 2249-2253 (2002).

Bankston, D. et al., "A scaleable synthesis of BAY 43-9006: A potent raf kinase inhibitor for the treatment of cancer," Organic Process Research & Development, 2002, vol. 6, pp. 777-781.

Bayer Pharmaceutics Corporation & Onxy Pharmaceutiacls, Inc., "Novel RAF kinase inhibitor Bay-43-9006 shows early signs of tolerability and activity in phase lb combination trials reported at ASCO," Jun. 2, 2003.

(Continued)

*Primary Examiner* — San-Ming Hui
*Assistant Examiner* — Kathrien Cruz
(74) *Attorney, Agent, or Firm* — Millen, White, Zelano & Branigan, P.C.

(57) ABSTRACT

The present invention relates to a novel form, thermodynamically stable at room temperature, of the tosylate salt of 4-{4-[({[4-chloro-3-(trifluoromethyl)phenyl]amino}carbonyl)amino]phenoxy}-N-methylpyridine-2-carboxamide, to processes for its preparation, to medicaments comprising it and to its use in the control of disorders.

31 Claims, 6 Drawing Sheets

(56) References Cited

U.S. PATENT DOCUMENTS

| | | | |
|---|---|---|---|
| 2011/0257035 A1 | 10/2011 | Pena et al. | |
| 2012/0040925 A1 | 2/2012 | Carter et al. | |
| 2012/0142741 A1 | 6/2012 | Schueckler | |
| 2012/0142742 A1 | 6/2012 | Riedl et al. | |
| 2013/0116442 A1 | 5/2013 | Stiehl | |
| 2013/0183268 A1 | 7/2013 | Christensen | |
| 2013/0261120 A1 | 10/2013 | Puhler et al. | |

FOREIGN PATENT DOCUMENTS

| | | |
|---|---|---|
| WO | WO-96 09045 | 3/1996 |
| WO | WO-98 11893 | 3/1998 |
| WO | WO 00/41698 | 7/2000 |
| WO | WO-00 42012 | 7/2000 |
| WO | WO 00/42012 A1 | 7/2000 |
| WO | WO 02/062763 A2 | 8/2002 |
| WO | WO-03 047579 | 6/2003 |
| WO | WO 03/050111 A1 | 6/2003 |
| WO | 03068228 | 8/2003 |
| WO | WO 03/068226 A1 | 8/2003 |
| WO | WO-03 068228 | 8/2003 |
| WO | WO 03/088228 A1 | 8/2003 |
| WO | WO-2005000284 | 1/2005 |
| WO | WO-2006 034796 | 4/2006 |
| WO | WO 2006/034797 A1 | 4/2006 |
| WO | WO-2006094626 | 9/2006 |
| WO | WO2013/000909 | 1/2013 |
| WO | WO2013/000917 | 1/2013 |

OTHER PUBLICATIONS

Fischer, S. et al., "Effect of astroglial cells on hypoxia-induced permeability of PBMEC cells," Am. J. Physiol. Cell Physiol., 2000, vol. 279, pp. C935-C944.

Fischer, S. et al., "Hypoxia induces permeability in brain microvessel endothelial cells via VEGF and NO," Am. J. Physiol. Cell Physiol., 1999, vol. 276, pp. C812-C820.

Heiss, J. D. et al., "Mechanism of dexamethasone suppression of brain tumor-associated vascular permeability in rats," The Journal of Clinical Investigation, Sep. 1996, vol. 98, No. 6, pp. 1400-1408.

Onyx Pharmaceuticals, Inc., "BAY 43-9006 data presented at 2002 AACR Meeting," Apr. 2, 2002.

Mross, K. et al., "Drug-drug pharmacokinetic study with Raf kinase inhibition (RKI) BAY-43-9006 administered in combination with irinotecan (CPT-11) in patients with solid tumors," International Journal of Clinical Pharmacology, 2003, vol. 41, No. 12, pp. 618-619.

WHO Drug Information, 2003, vol. 17, No. 4, list 50.

Pharma Tech Japan "Physico-chemical studies on the molecuiar details of crystals (12) Optimization of salt/crystal form and crystallization technology"; vol. 18 No. 10 (2002), pp. 1629-1645.

Pharma Tech Japan "Kazuhide Ashizewa, Department of Physical Chemistry: Tsukuba Research Laboratories, Eisai Co., Ltd.,"; vol. 10 No. 10 (2002), pp. 1629-1644.

Opposition of corresponding EP Patent 1797038 by Blofer S.P.A. Mar. 13, 2013.

Opposition of corresponding EP Patent 1797038 by Fresenlus Kabl Deutschland GmbH Mar. 12, 2013.

(EMEA) Scientific Discussion of Nexavar (2008).

EMEA, Summary of Product Characteristics of Nexavar (2012).

Nexavar Approval letter by FDA Dec. 20, 2005.

S. Byrn et al., Pharmaceutical Research, Jul. 1995, 12(7) pp. 945-954.

M. Bavin, Chemistry & Industry, Aug. 21, 1989, pp. 527-528.

Hotto, Hirte et al., "BAY 43-9006 Early Clinical Data in Patients with Advanced Solid Malignancies", 2002, 5, pp. 2249-2253.

Hilger et al., "Circadian rhythm in the regulation of MAP kinase pathway—pitfall in the determination of surrogate parameters" International Journal of Clinical Pharmacotogy & Therapeutics, vol. 41, Dec. 2003.

Lyons et al., "Discovery of a novel Raf kinase inhibitor" Endocrine-Related Cancer 2001, vol. 8 2001, pp. 219-225.

Ahmad Elsen "Kinase inhibition with BAY 43-9006 in Renal Cell Carcinoma" Clinical Cancer Research, vol. 10, Sep. 15, 2004.

EMEA Sorafenib Scientific Discussion 4 pages, 2008.

Spectral Data D-9 to D13 Mar. 12, 2013.

Spectral Data D-14 to D18 Mar. 12, 2013.

Declarations of Sandeep Kaur, Varun Sharma and Nikunj Kachhadia Mar. 12, 2010.

Reply to First Office Action dated February 10, 2010.

Opposition of corresponding EP Patent 1797038 by Fresenius Kabi Deutschland GmbH Mar. 12, 2013.

(EMEA) Scientific Discussion of Nexavar (2006).

M. Savin, Chemistry & Industry, Aug. 21, 1989, pp. 527-529.

Hotte, Hirte et al., "BAY 43-9006 Early Clinical Data in Patients with Advanced Solid Malignancies", 2002, 8, pp. 2249-2253.

Hilger et al., "Circadian rhythm in the regulation of MAP kinase pathway—pitfall in the determination of surrogate parameters" International Journal of Clinical Pharmacology & Therapeutics, vol. 41, Dec. 2003.

Ahmad Eisen "Kinase inhibition with BAY 43-9006 in Renal Cell Carcinoma" Clinical Cancer Research, vol. 10, Sep. 15, 2004.

EMEA Sorafenib Scientific Discussion 4 pages, 2006.

Declarations of Sandeep Kaur, Varun Sharma and Nikunj Kachhadia Mar. 12, 2013.

Reply to First Office Action dated Feb. 10, 2010.

Document D30 of European Opposition of EP 1797038; excerpt of Integrated protocol of the phase III study. 2005.

Document D32 of European Opposition of EP 1797038; submission dated Sep. 27, 2010 in the examination proceedings of the patent in dispute. 2010.

Document D27 of European Opposition of EP 1797038; x-ray diffractogram of the retained sample of Example 1 according to the patent in dispute.

Document D28 of European Opposition of EP 1797038; Duntz et al: "Disappearing Polymorphs", Acc. Chem. Res., vol. 28, 1995, pp. 193-200.

Document D29 of European Opposition of EP 1797038; excerpt of Clinical study protocol of the phase II study.

Document D30 of European Opposition of EP 1797038; excerpt of Integrated protocol of the phase III study.

Document D31 of European Opposition of EP 1797038; excerpt of presentation "Handling of Study Drug Medication/IVRS" by study manager Jeanne Lewis, dated Oct. 31, 2013

Wilhelm et al., Current Pharmaceutical Design, "Bay 43-9006: Preclinical Data", 2002, vol. 8, pp. 2255-2257.

Carstensen T., Advanced Pharmaceutical Solids, 2001, pp. 117-131.

Patentees Response in European Opposition of EP 1797038 dated Oct. 31, 2013.

Document D27 of European Opposition of EP 1797038; x-ray diffractogram of the retained sample of Example 1 according to the patent in dispute. 2013.

Document D28 of European Opposition of EP 1797038; Duntz et al; "Disappearing Polymorphs", Acc. Chem. Res., vol. 28, 1995, pp. 193-200.

Document D29 of European Opposition of EP 1797038; excerpt of Clinical study protocol of the phase II study. 2002.

Document D30 of European Opposition of EP 1797038; excerpt of Integrated protocol of the phase III study. 2003.

Document D32 of European Opposition of EP 1797038; submission dated Sep. 27, 2010 in the examination proceedings of the patent in dispute.

\* cited by examiner

THERMODYNAMICALLY STABLE FORM OF A TOSYLATE SALT

RELATED APPLICATIONS/PATENTS AND INCORPORATION BY REFERENCE

This application is a National Stage Application filed under 35 U.S.C. §371 based on International Application No. PCT/EP2005/010119, filed Sep. 20, 2005, which claims priority to European Patent Application Number 04023130.0, filed Sep. 29, 2004, the entire contents each of which are incorporated herein by reference.

The foregoing applications, and all documents cited therein and all documents cited or referenced therein, and all documents cited or referenced herein, including any U.S. or foreign patents or published patent applications, International patent applications, as well as, any non-patent literature references and any manufacturer's instructions, are hereby expressly incorporated herein by reference.

The present invention relates to a novel form, thermodynamically stable at room temperature, of the tosylate salt of 4-{4-[({[4-chloro-3-(trifluoromethyl)phenyl]amino}carbonyl)amino]phenoxy}-N-methylpyridine-2-carboxamide, to processes for its preparation, to pharmaceutical compositions comprising it and to its use in the control of disorders.

The tosylate salt of 4-{4-[({[4-chloro-3-(trifluoromethyl)phenyl]amino}carbonyl)amino]phenoxy}-N-methylpyridine-2-carboxamide is mentioned in WO 03/068228 and WO 03/047579 and corresponds to the compound of the formula (I):

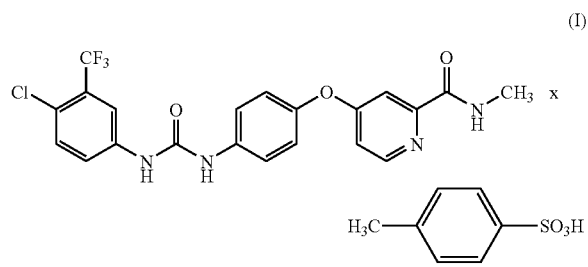

WO 03/068228 relates, inter alia, to the use of the compound of the formula (I) for the treatment of disorders in which angiogenesis plays an important role, for example in tumor growth. WO 03/047579 relates to arylureas in combination with cytotoxic or cytostatic compounds for the treatment of cancer.

The compound 4-{4-[({[4-chloro-3-(trifluoromethyl)phenyl]amino}carbonyl)amino]phenoxy}-N-methylpyridine-2-carboxamide is described in WO 00/42012 and corresponds to the compound of the formula (II):

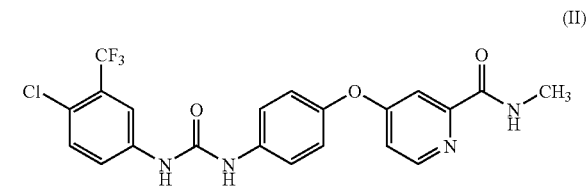 [SMILES: CNC(=O)c1cc(Oc2ccc(NC(=O)Nc3ccc(Cl)c(C(F)(F)F)c3)cc2)ccn1]

The compounds and their salts, disclosed in WO 00/42012, for example tosylates, are described there as inhibitors of the enzyme Raf kinase and may be used for the treatment of disorders, for example cancer.

The compound of the formula (II) is prepared in the manner described in WO 00/42012. The compound of the formula (I) is prepared according to a general standard method for the preparation of tosylate salts, as described in example 1 of the working examples. In this method, the compound of the formula (I) is obtained in one crystal polymorph which is referred to hereinbelow as polymorph II. Polymorph II has a transition point of 194° C. and a characteristic X-ray diffractogram, IR spectrum, Raman spectrum, FIR spectrum and NIR spectrum (Tab. 1-6, FIG. 1-6). It has been found that polymorph II is metastable.

Surprisingly, two further polymorphs and two solvates of the compound of the formula (I) have been found. The compound of the formula (I) in the polymorph I melts under decomposition at 223-231° C., the compound of the formula (I) in the polymorph III melts at 187-190° C. The monomethanol solvate of the compound of the formula (I) contains 4.8% methanol and the monoethanol solvate of the compound of the formula (I) 6.7% ethanol. The inventive polymorph I of the compound of the formula (I) is thermodynamically stable at room temperature and is storage-stable even after processing via suspensions and is therefore particularly suitable for use in pharmaceutical formulations, for example suspensions or creams, but also in other preparations which are prepared via suspended active ingredient, for example in aqueous granulation or wet grinding.

The present invention provides the compound of the formula (I) in the polymorph I. The inventive use of the compound of the formula (I) in the stable polymorph I ensures that an undesired conversion to another polymorph and an associated change in the properties of the compound of the formula (I), for example solubility or bioavailability, are prevented. This increases the safety and quality of preparations comprising the compound of the formula (I) and the risk to the patient is reduced.

Figure 1:
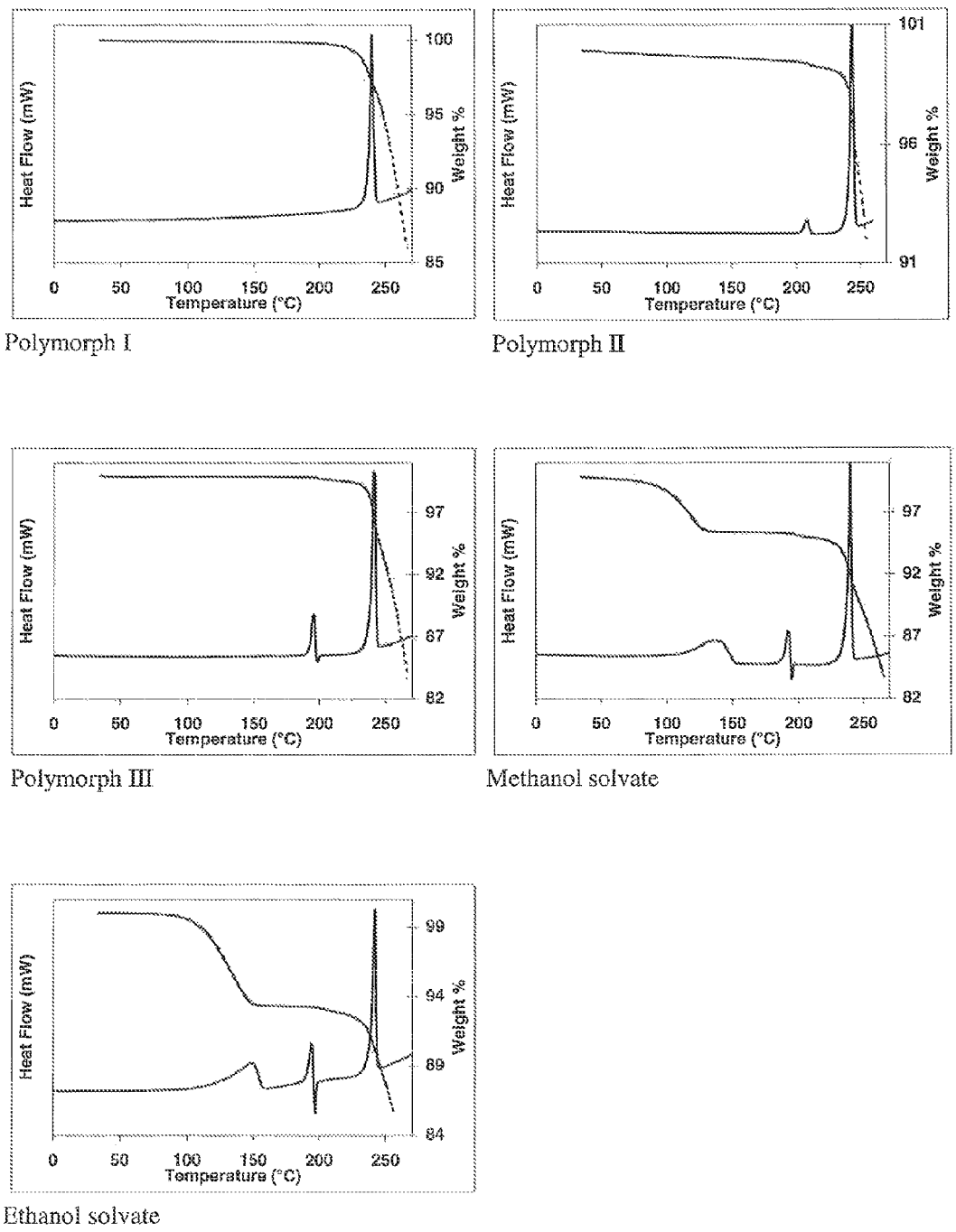
FIG. 1 is DSC—and TGA-thermograms of compound (I).
Figure 2:
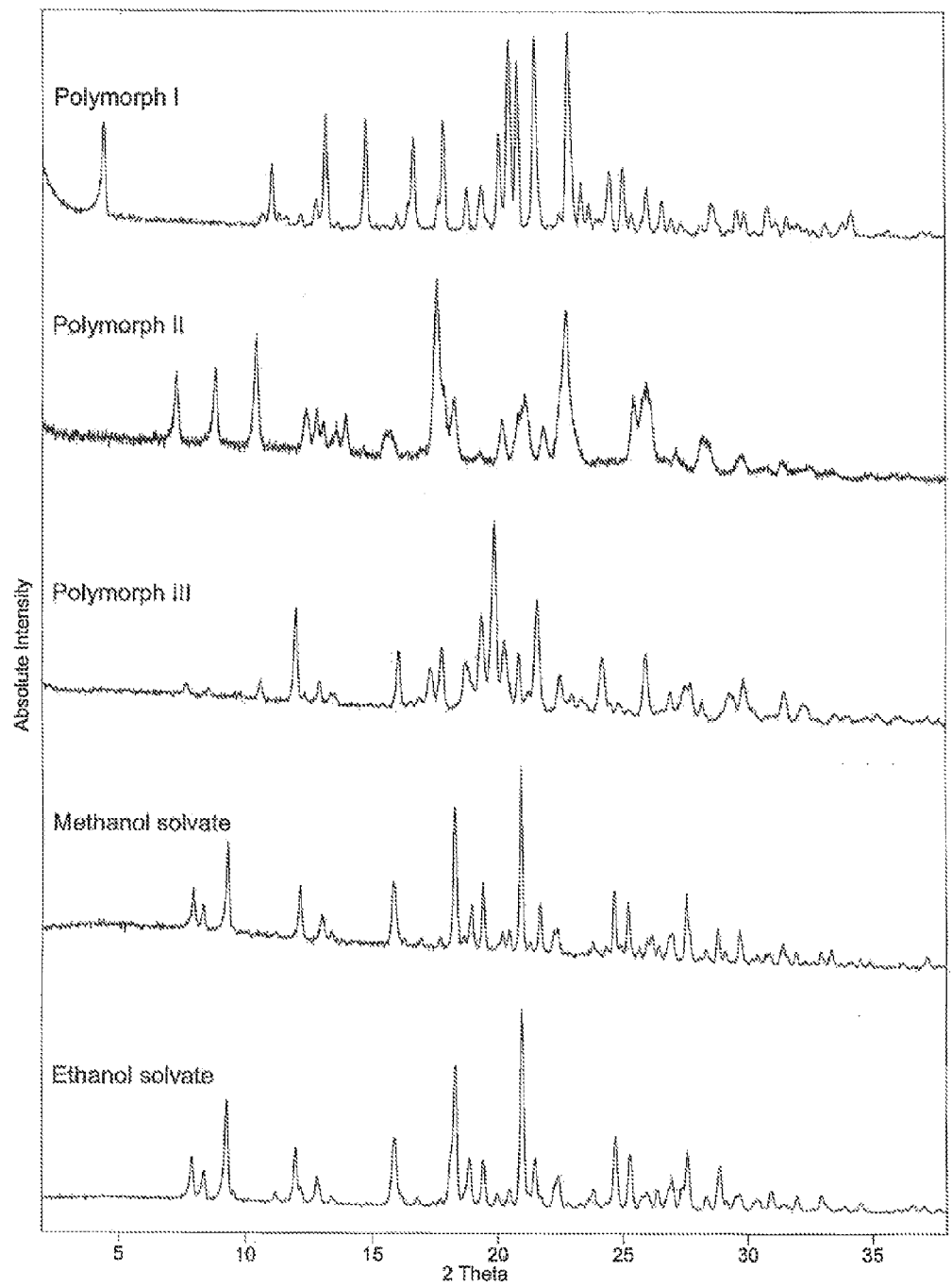
FIG. 2 is X-Ray diffraction patterns of compound (I).
Figure 3:
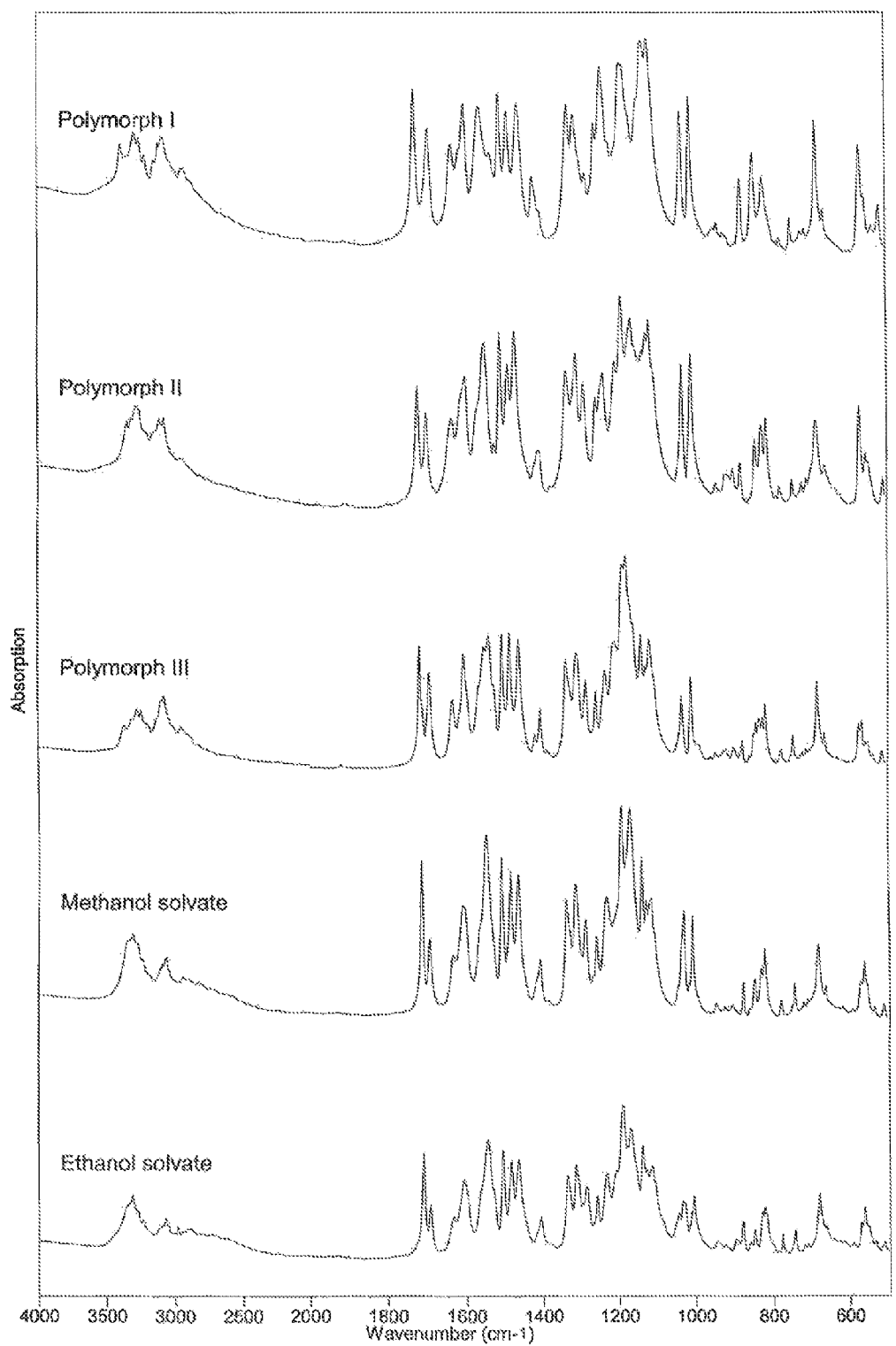
FIG. 3 is IR spectra of compound (I).
Figure 4:
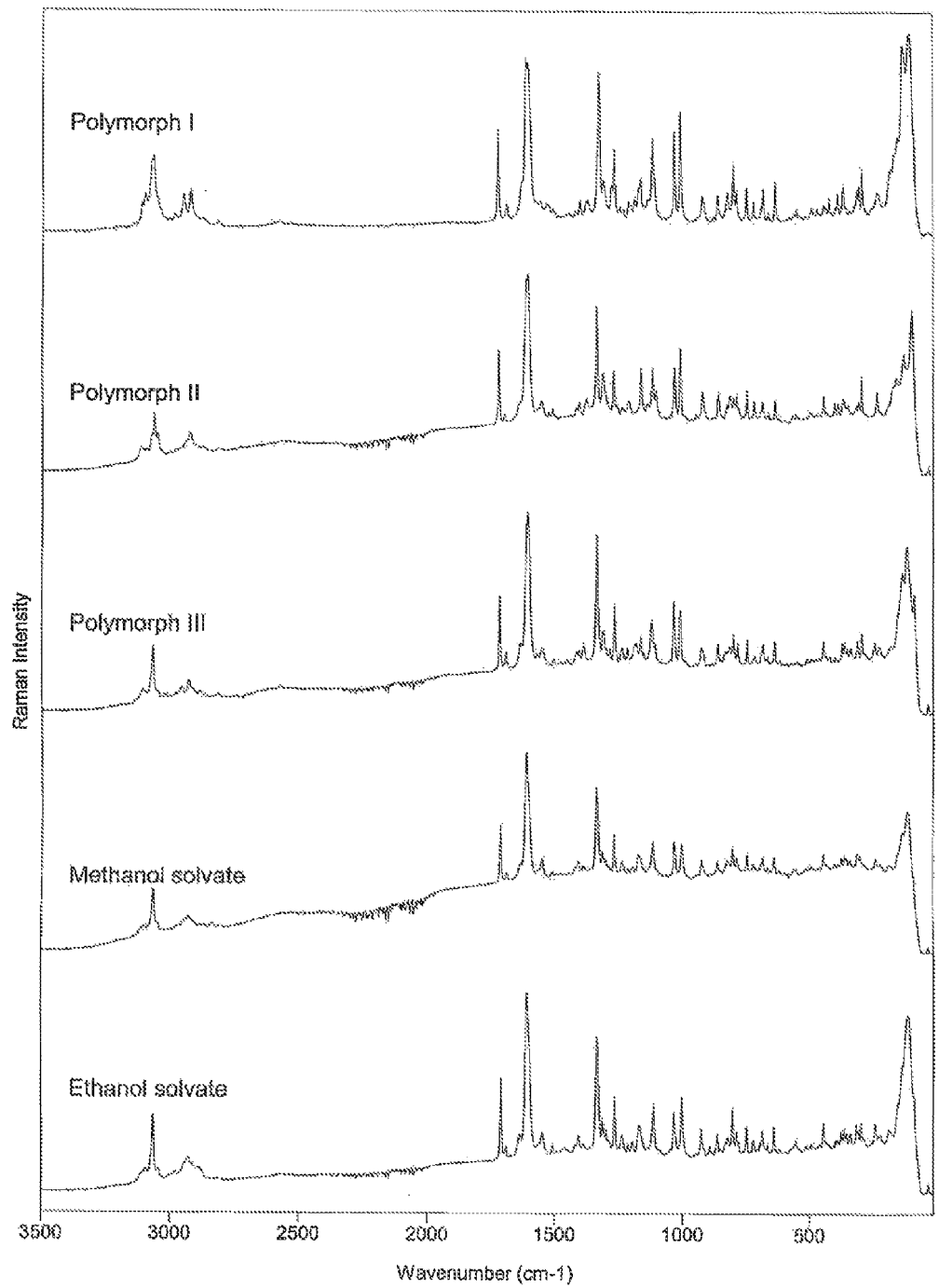
FIG. 4 is Raman spectra of compound (I).
Figure 5:
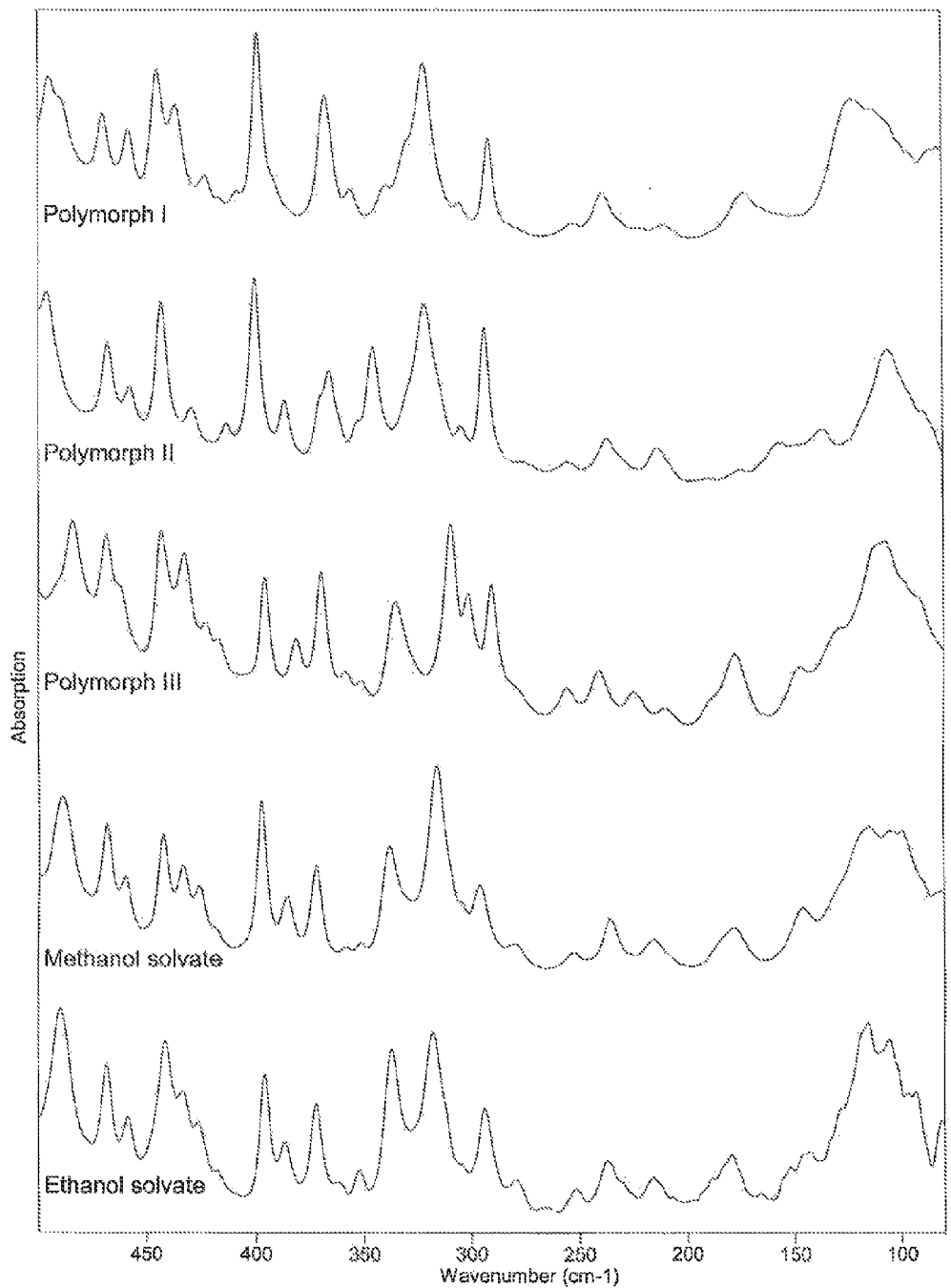
FIG. 5 is FIR spectra of compound (I).
Figure 6:
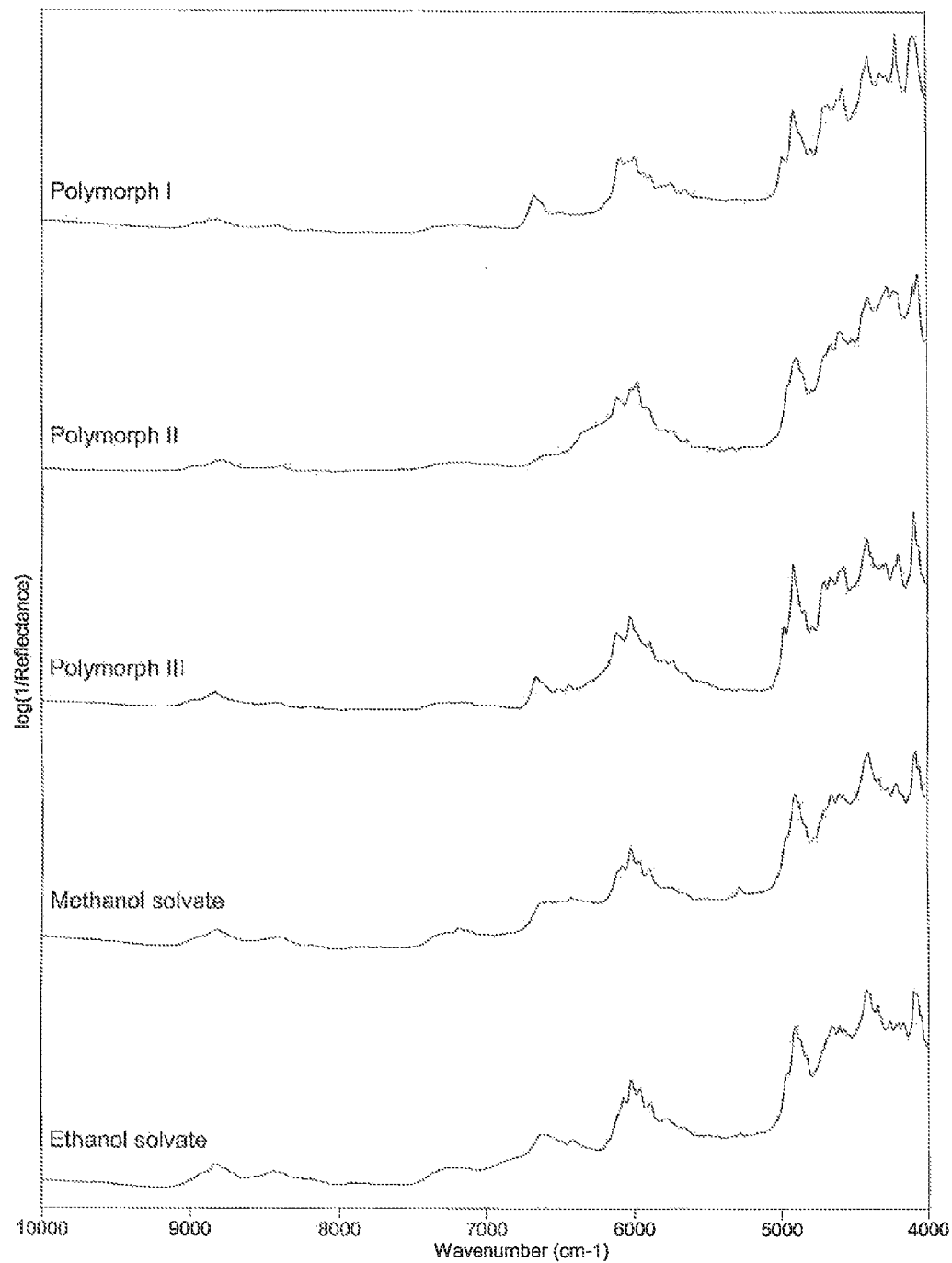
FIG. 6 is NIR spectra of compound (I).

Polymorph I of the compound of the formula (I), in comparison to polymorph II, polymorph III, the ethanol and methanol solvate, has a clearly differentiable X-ray diffractogram, NIR spectrum, FIR spectrum and Raman spectrum (FIG. 2-6). The compound of the formula (I) in the polymorph I melts under decomposition at 223-231° C. and is thus clearly differentiable from polymorph II (conversion point 194° C.) and polymorph III (melting point 187-190° C.). Unlike those solvent-free forms, the ethanol solvate of the compound of the formula (I) and the methanol solvate of the compound of the formula (I) have losses of mass in thermogravimetric analysis (TGA) of 6.7% and 4.8% respectively (FIG. 1).

The inventive compound of the formula (I) in the polymorph I is used in high purity in pharmaceutical formulations. For reasons of stability, a pharmaceutical formulation comprises the compound of the formula (I) mainly in the polymorph I and no significant fractions of another form, for example of another polymorph or of a solvate of the compound of the formula (I). The pharmaceutical composition preferably contains more than 90 percent by weight, more preferably more than 95 percent by weight, of the compound of the formula (I) in the polymorph I related to the total amount of the compound of the formula (I) present in the composition.

Method for Treatment:

The present invention further provides the use of the compound of the formula (I) in the polymorph I for the treatment of disorders. Preference is given to using it for the treatment of disorders which feature abnormal angiogenesis or hyperpermeability processes, bone marrow diseases, for example leukemia, or treatment of carcinoma, for example carcinoma of the lung, of the pancreas, of the thyroid gland, of the kidney or of the intestine, or for the treatment of carcinogenic cell growth.

The present invention further provides the use of the compound of the formula (I) in the polymorph I for the preparation of a pharmaceutical composition for the treatment of disorders. Preference is given to using it for the treatment of disorders which feature abnormal angiogenesis or hyperpermeability processes, bone marrow diseases, for example leukemia, or treatment of carcinoma, for example carcinoma of the lung, of the pancreas, of the thyroid gland, of the kidney or of the intestine, or for the treatment of carcinogenic cell growth.

The compound of the formula (I) in the polymorph I of the present invention can be used to treat, modulate and/or prevent any disease or condition mediated by one or more cellular signal transduction pathways involving raf, VEGFR, PDGFR, p38, and/or flt-3 kinases.

The term "mediated" indicates, e.g., that the signaling molecule is part of the pathway which is aberrant or disturbed in the disease and/or condition.

While not wishing to be bound by any theory or mechanism of action, it has been found that compounds of the present invention possess the ability to modulate raf, VEGFR, PDGFR, p38, and/or flt-3 kinase activity. The methods of the present invention, however, are not limited to any particular mechanism or how the compounds achieve their therapeutic effect.

By the term "modulate," it is meant that the functional activity of the pathway (or a component of it) is changed in comparison to its normal activity in the absence of the compound. This effect includes any quality or degree of modulation, including, increasing, agonizing, augmenting, enhancing, facilitating, stimulating, decreasing, blocking, inhibiting, reducing, diminishing, antagonizing, etc.

By the phrase "kinase activity," it is meant a catalytic activity in which a phosphate from adenosine triphosphate (ATP) is transferred to an amino acid residue (e.g., serine, threonine, or tyrosine) in a protein substrate. A compound can modulate kinase activity, e.g., inhibiting it by directly competing with ATP for the ATP-binding pocket of the kinase, by producing a conformational change in the enzyme's structure that affects its activity (e.g., by disrupting the biologically-active three-dimensional structure), etc. Kinase activity can be determined routinely using conventional assay methods. Kinase assays typically comprise the kinase enzyme, substrates, buffers, and components of a detection system.

A disease or condition "mediated" by raf, VEGFR, PDGFR, p38, and/or flt-3 indicates that one of these receptors is a part of a signal transduction pathway that is involved in any aspect of the disease phenotype (e.g., where a defect in the receptor itself is involved in "causing" the disease; where stimulation of the receptor by its ligand induces cell motility, migration, and/or proliferation that produces a disease phenotype; where receptor stimulation or phosphorylation results in restonosis; any functional activity of raf, VEGFR, PDGFR, p38, and/or flt-3 that, when inappropriately expressed, results in a disease symptom and/or phenotype).

The term "treating" is used conventionally, e.g., the management or care of a subject for the purpose of combating, alleviating, reducing, relieving, improving the condition of, etc., of a disease or disorder.

Diseases and conditions that can be treated include any of those mentioned above and below, as well as:

Raf associated diseases include, e.g., cell-proliferation disorders, cancer, tumors, etc.;

VEGFR-2 associated diseases include, e.g., cancer, tumor growth, inflammatory disease, rheumatoid arthritis, retinopathy, psoriasis, glomerulonephritis, asthma, chronic bronchitis, atherosclerosis, transplant rejection, conditions involving angiogenesis, etc.;

VEGFR-3 associated diseases include, e.g., cancer, corneal disease, inflamed cornea, corneal transplantation, lymphatic hyperplasia, conditions involving lymphangiogenesis, etc.;

PDGFR-beta associated diseases include, e.g., diseases or conditions characterized by cell proliferation, cell matrix production, cell movement, and/or extracellular matrix production. Specific examples, include, e.g., tumors, malignancies, cancer, metastasis, chronic myeloid leukemia, inflammation, renal disease, diabetic nephropathy, mesangial proliferative glomerulonephritis, fibrotic conditions, atherosclerosis, restenosis, hypertension-related arteriosclerosis, venous bypass graft arteriosclerosis, scleroderma, interstitial pulmonary diseases, synovial disorders, arthritis, leukemias, lymphomas, etc;

Flt-3 associated diseases include, e.g., immune-related disorders, blood cell disorders, conditions involving hematopoietic cell development (e.g., T-cells, B-cells, dendritic cells, cancer, anemia, HIV, acquired immune deficiency syndrome, etc.

p38 associated diseases include inflammatory disorders, immunomodulatory disorders, and other disorders that have been linked to abnormal cytokine production, especially TNF-alpha, or abnormal MMP activity. These disorders include, but are not limited to, rheumatoid arthritis, COPD, osteoporosis, Crohn's disease and psoriasis.

Methods of the present invention include modulating tumor cell proliferation, including inhibiting cell proliferation. The latter indicates that the growth and/or differentiation of tumor cells is reduced, decreased, diminished, slowed, etc. The term "proliferation" includes any process which relates to cell growth and division, and includes differentiation and apoptosis. As discussed above, raf kinases play a key role in the activation of the cytoplasmic signaling cascade involved in cell proliferation, differentiation, and apoptosis. For example, studies have found that inhibiting c-raf by anti-sense oligonucleotides can block cell proliferation. Any amount of inhibition is considered therapeutic.

Methods of the present invention also include treating mammalian hyper-proliferative disorders. Hyper-proliferative disorders include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Any tumor or cancer can be treated, including, but not limited to, cancers having one or more mutations in raf, ras, VEFGR, PDGFR, p38, and/or flt-3, as well as any upstream or downstream member of the signaling pathways of which they are a part. As discussed earlier, a cancer can be treated with a compound of the present invention irrespective of the mechanism which is responsible for it.

Cancers of any organ can be treated, including cancers of, but are not limited to, e.g., colon, pancreas, breast, prostate, bone, liver, kidney, lung, testes, skin, pancreas, stomach, colorectal cancer, renal cell carcinoma, hepatocellular carcinoma, melanoma, etc.

Examples of breast cancer include, but are not limited to, invasive ductal carcinoma, invasive lobular carcinoma, ductal carcinoma in situ, and lobular carcinoma in situ.

Examples of cancers of the respiratory tract include, but are not limited to, small-cell and non-small-cell lung carcinoma, as well as bronchial adenoma and pleuropulmonary blastoma.

Examples of brain cancers include, but are not limited to, brain stem and hypophtalmic glioma, cerebellar and cerebral astrocytoma, medulloblastoma, ependymoma, as well as neuroectodermal and pineal tumor.

Tumors of the male reproductive organs include, but are not limited to, prostate and testicular cancer. Tumors of the female reproductive organs include, but are not limited to, endometrial, cervical, ovarian, vaginal, and vulvar cancer, as well as sarcoma of the uterus.

Tumors of the digestive tract include, but are not limited to, anal, colon, colorectal, esophageal, gallbladder, gastric, pancreatic, rectal, small-intestine, and salivary gland cancers.

Tumors of the urinary tract include, but are not limited to, bladder, penile, kidney, renal pelvis, ureter, and urethral cancers.

Eye cancers include, but are not limited to, intraocular melanoma and retinoblastoma.

Examples of liver cancers include, but are not limited to, hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to, squamous cell carcinoma, Kaposi's sarcoma, malignant melanoma, Merkel cell skin cancer, and non-melanoma skin cancer.

Head-and-neck cancers include, but are not limited to, laryngeal, hypopharyngeal, nasopharyngeal, and/or oropharyngeal cancers, and lip and oral cavity cancer.

Lymphomas include, but are not limited to, AIDS-related lymphoma, non-Hodgkin's lymphoma, cutaneous T-cell lymphoma, Hodgkin's disease, and lymphoma of the central nervous system.

Sarcomas include, but are not limited to, sarcoma of the soft tissue, osteosarcoma, malignant fibrous histiocytoma, lymphosarcoma, and rhabdomyosarcoma.

Leukemias include, but are not limited to, acute or chronic, acute myeloid leukemia, acute lymphoblastic leukemia, acute Lymphocytic Leukemia, chronic lymphocytic leukemia, chronic myelogenous leukemia, hairy cell leukemia, undifferentiated AML, promyelocytic leukemia, myelomonocytic leukemia, monocytic leukemia, or erythroleukemia, megakaryoblastic leukemia, etc.

In addition to inhibiting the proliferation of tumor cells, compounds of the present invention can also cause tumor regression, e.g., a decrease in the size of a tumor, or in the extent of cancer in the body.

The present invention also relates to methods of modulating angiogenesis and/or lymphangiogenesis in a system comprising cells, comprising administering to the system an effective amount of a compound described herein. A system comprising cells can be an in vivo system, such as a tumor in a patient, isolated organs, tissues, or cells, in vitro assays systems (CAM, BCE, etc), animal models (e.g., in vivo, subcutaneous, cancer models), hosts in need of treatment (e.g., hosts suffering from diseases having angiogenic and/or lymphangiogenic component, such as cancer), etc.

Inappropriate and ectopic expression of angiogenesis (e.g., abnormal angiogenesis) can be deleterious to an organism. A number of pathological conditions are associated with the growth of extraneous blood vessels. These include, e.g., diabetic retinopathy, neovascular glaucoma, psoriasis, retrolental fibroplasias, angiofibroma, inflammation, etc. In addition, the increased blood supply associated with cancerous and neoplastic tissue, encourages growth, leading to rapid tumor enlargement and metastasis. Moreover, the growth of new blood and lymph vessels in a tumor provides an escape route for renegade cells, encouraging metastasis and the consequence spread of the cancer.

Methods of the present invention also relate to treating and/or preventing disorders or conditions associated with, or resulting from, vascular hyperpermeability.

For example, VEGF increases endothelial cell permeability. As a consequence, any condition which results in the release of VEGF, especially in higher than normal amounts, can be associated with vascular hyperpermeability and its accompanying deleterious effects. The present invention, however, provides for the treatment or prevention of any condition or disorder associated with, or resulting from, vascular hyperpermeability, regardless of the mechanism of action.

Edema formation is a life-threatening complication of various diseases of the central nervous system, including head injury, tumors, stroke, hypoxia, and high altitude sickness. The underlying cause of edema is vascular hyperpermeability. Compounds of the present invention can be utilized to treat and/or prevent vascular hyperpermeability, thereby treating and/or preventing edema, and the deleterious effects associated with it.

Other hyperpermeability conditions (or conditions that produce vascular hypermeability), include, but are not limited to, tissue edema (e.g., lung, kidney, brain, etc.), vasogenic brain edema, chronic inflammation, wound healing, ischemia, tumors, atherosclerosis, peripheral vascular disease, ascites, effusions, exudates, nephrotic edema, primary glomerular disease, peripheral artery disease, diabetic retinopathy, diabetic retinal disease, obstruction of respiratory airways during asthma and other pulmonary disorders, circulatory collapse in sepsis, acute lung injury, acute respiratory distress syndrome, etc.

Assays for vascular permeability can be done routinely, e.g., Heiss et al., J. Clin. Invest., 98:1400-1408, 1996; Fischer et al., Am. J. Physiol., 276(4 Pt 1):C812-20, 1999; Fischer et al., Am. J. Physiol. Cell. Physiol., 279:C935-C944, 2000.

The compound of the formula (I) in the polymorph I of this invention also has a broad therapeutic activity to treat or prevent the progression of a broad array of diseases, such as inflammatory conditions, coronary restenosis, tumor-associated angiogenesis, atherosclerosis, autoimmune diseases, inflammation, certain kidney diseases associated with proliferation of glomerular or mesangial cells, and ocular diseases associated with retinal vessel proliferation. psoriasis, hepatic cirrhosis, diabetes, atherosclerosis, restenosis, vascular graft restenosis, in-stent stenosis, angiogenesis, ocular diseases, pulmonary fibrosis, obliterative bronchiolitis, glomerular nephritis, rheumatoid arthritis.

The present invention also provides for treating, preventing, modulating, etc., one or more of the following conditions in humans and/or other mammals: retinopathy, including diabetic retinopathy, ischemic retinal-vein occlusion, retinopathy of prematurity and age related macular degeneration; rheumatoid arthritis, psoriasis, or bullous disorder associated with subepidermal blister formation, including bullous pemphigoid, erythema multiforme, or dermatitis herpetiformis, rheumatic fever, bone resorption, postmenopausal osteoporosis, sepsis, gram negative sepsis, septic shock, endotoxic shock, toxic shock syndrome, systemic inflammatory response syndrome, inflammatory bowel disease (Crohn's disease and ulcerative colitis), Jarisch-Herxheimer reaction, asthma, adult respiratory distress syndrome, acute pulmonary fibrotic disease, pulmonary sarcoidosis, allergic respiratory disease, silicosis, coal worker's pneumoconiosis, alveolar injury, hepatic failure, liver disease during acute inflammation, severe alcoholic hepatitis, malaria (*Plasmodium falciparum* malaria and cerebral malaria), non-insulin-dependent diabetes mellitus (NIDDM), congestive heart failure, damage following heart disease, atherosclerosis, Alzheimer's disease, acute encephalitis, brain injury, multiple sclerosis (demyelation and oligiodendrocyte loss in multiple sclerosis), advanced cancer, lymphoid malignancy, pancreatitis, impaired wound healing in infection, inflammation and cancer, myelodysplastic syndromes, systemic lupus erythematosus, biliary cirrhosis, bowel necrosis, radiation injury/toxicity following administration of monoclonal antibodies, host-versus-graft reaction (ischemia reperfusion injury and allograft rejections of kidney, liver, heart, and skin), lung allograft rejection (obliterative bronchitis), or complications due to total hip replacement, ad an infectious disease selected from tuberculosis, *Helicobacter pylori* infection during peptic ulcer disease, Chaga's disease resulting from *Trypanosoma cruzi* infection, effects of Shiga-like toxin resulting from *E. coli* infection, effects of enterotoxin A resulting from *Staphylococcus* infection, meningococcal infection, and infections from *Borrelia burgdorferi, Treponema pallidum*, cytomegalovirus, influenza virus, Theiler's encephalomyelitis virus, and the human immunodeficiency virus (HIV), papilloma, blastoglioma, Kaposi's sarcoma, melanoma, lung cancer, ovarian cancer, prostate cancer, squamous cell carcinoma, astrocytoma, head cancer, neck cancer, bladder cancer, breast cancer, colorectal cancer, thyroid cancer, pancreatic cancer, gastric cancer, hepatocellular carcinoma, leukemia, lymphoma, Hodgkin's disease, Burkitt's disease, arthritis, rheumatoid arthritis, diabetic retinopathy, angiogenesis, restenosis, in-stent restenosis, vascular graft restenosis, pulmonary fibrosis, hepatic cirrhosis, atherosclerosis, glomerulonophritis, diabetic nephropathy, thrombic micoangiopathy syndromes, transplant rejection, psoriasis, diabetes, wound healing, inflammation, and neurodegenerative diseases. hyperimmune disorders, hemangioma, myocardial angiogenesis, coronary and cerebral collateral vascularization, ischemia, corneal disease, rubeosis, neovascular glaucoma, macular degeneration retinopathy of prematurity, wound healing, ulcer *Helicobacter* related diseases, fractures, endometriosis, a diabetic condition, cat scratch fever, thyroid hyperplasia, asthma or edema following burns, trauma, chronic lung disease, stroke, polyps, cysts, synovitis, chronic and allergic inflammation, ovarian hyperstimulation syndrome, pulmonary and cerebral edema, keloid, fibrosis, cirrhosis, carpal tunnel syndrome, adult respiratory distress syndrome, ascites, an ocular condition, a cardiovascular condition, Crow-Fukase (POEMS) disease, Crohn's disease, glomerulonophritis, osteoarthritis, multiple sclerosis, graft rejection, Lyme disease, sepsis, von Hippel Lindau disease, pemphigoid, Paget's disease, polycystic kidney disease, sarcoidosis, throiditis, hyperviscosity syndrome, Osler-Weber-Rendu disease, chronic occlusive pulmonary disease, radiation, hypoxia, preeclampsia, menometrorrhagia, endometriosis, infection by Herpes simplex, ischemic retinopathy, corneal angiogenesis, Herpes Zoster, human immunodeficiency virus, parapoxvirus, protozoa, toxoplasmosis, and tumor-associated effusions and edema.

The present invention further provides a method for the prevention or treatment of diseases, especially of the aforementioned diseases, using an effective amount of the compound of the formula (I) in the polymorph I.

Combination with Other Pharmaceutical Agents:

The compound of the formula (I) in the polymorph I of this invention can be administered as the sole pharmaceutical agent or in combination with one or more other pharmaceutical agents where the combination causes no unacceptable adverse effects. This may be of particular relevance for the treatment of hyper-proliferative diseases such as cancer. In this instance, the compound of this invention can be combined with known cytotoxic agents, signal transduction inhibitors, with other anti-cancer agents, or with antiemetics, as well as with admixtures and combinations thereof.

In one embodiment, the compound of the formula (I) in the polymorph I of the present invention can be combined with cytotoxic anti-cancer agents. Examples of such agents can be found in the 11th Edition of the Merck Index (1996). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds of the invention include, but are not limited to, those compounds acknowledged to be used in the treatment of neoplastic diseases in Goodman and Gilman's The Pharmacological Basis of Therapeutics (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

In another embodiment, the compound of the formula (I) in the polymorph I of the present invention can be combined with antiemetics. Antiemetics suitable for use with the compounds of the invention include, but are not limited to, antihistamines, $H_1$ receptor blockers, 5-$HT_3$ antagonists, neuroleptics, anticholinergics, dopamine antagonists, serotonin antagonists, glucocorticoids or cannabinoids. These agents include, by no way of limitation, meclozin, dimenhydrinate, phenothiazin derivatives (e.g. thiethylperazin, triflupromazin), benzamide or benzimidazolon derivatives (e.g. metoclopramid, bromoprid, domperidon), butyrophenones, scopalamin, pyridoxine, chlorphenoxamin, granisetron, ondansetron, tropisetron, and dexamethason. Preference is given to the antiemetics: granisetron, ondansetron, tropisetron, or dexamethason.

"Combination" mean for the purposes of the invention not only a dosage form which contains all the components (so-called fixed combinations), and combination packs containing the components separate from one another, but also components which are administered simultaneously or sequentially, as long as they are employed for the prophylaxis or treatment of the same disease.

The active ingredients of the combination according to the invention can be converted in a known manner into the usual formulations, which may be liquid or solid formulations. Examples are tablets, coated tablets, pills, capsules, granules, aerosols, syrups, emulsions, suspensions, solutions.

Since the combination according to the invention is well tolerated and in some cases is effective even in low dosages, a wide range of formulation variants is possible. Thus, one possibility is to formulate the individual active ingredients of the combination according to the invention separately. In this case, it is not absolutely necessary for the individual active ingredients to be taken at the same time; on the contrary, sequential intake may be advantageous to achieve optimal effects. It is appropriate with such separate administration to combine the formulations of the individual active ingredients, for example tablets or capsules, simultaneously together in a suitable primary packaging. The active ingredients are present in the primary packaging in each case in separate containers which may be, for example, tubes, bottles or blister packs. Such separate packaging of the components in the joint primary packaging is also referred to as a kit.

Further formulation variants which are suitable and preferred for the combination according to the invention are also fixed combinations. "Fixed combination" is intended here to mean pharmaceutical forms in which the components are present together in a fixed ratio of amounts. Such fixed combinations may be, for example, in the form of oral solutions, but they are preferably solid oral pharmaceutical preparations, e.g. capsules or tablets.

Pharmaceutical Compositions:

This invention also relates to pharmaceutical compositions containing the compound of the formula (I) in the polymorph I of the present invention and methods of administering to a patient in need thereof a pharmaceutical composition of this invention.

A patient, for the purpose of this invention, is a mammal, including a human, in need of treatment for the particular condition or disease.

The pharmaceutical compositions of the present invention are comprised of a pharmaceutically acceptable carrier and a pharmaceutically effective amount of the compound of the formula (I) in the polymorph I of the present invention.

A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient.

A pharmaceutically effective amount of compound is that amount which produces a result or exerts an influence on the particular condition being treated.

The compound of the formula (I) in the polymorph I may be administered in a suitable manner, for example by the oral, parenteral, pulmonary, nasal, sublingual, lingual, buccal, rectal, dermal, transdermal, conjunctival or optic route, or as an implant or stent.

For these application routes, the inventive compounds may be administered in suitable administration forms.

For oral administration, suitable administration forms are those which function according to the prior art and deliver the compound of the formula (I) in the polymorph I in a rapid and/or modified manner, for example tablets (noncoated or coated tablets, for example with coatings which are resistant to gastric juice or have retarded dissolution or are insoluble and which control the release of the inventive compound), tablets which disintegrate rapidly in the oral cavity or films/wafers, films/lyophilizates, capsules (for example hard or soft gelatin capsules), sugar-coated tablets, granules, pellets, powders, suspensions or aerosols.

Parenteral administration can take place with avoidance of an absorption step (for example in an intravenous, intraarterial, intracardiac, intraspinal or intralumbar manner) or with inclusion of an absorption (for example in an intramuscular, subcutaneous, intracutaneous, percutaneous or intraperitoneal manner). Administration forms suitable for parenteral application include injection and infusion preparations in the form of suspensions, lyophilizates or sterile powders.

Suitable for the other administration routes are, for example, medicinal forms for inhalation (including powder inhalers, nebulizers), tablets for lingual, sublingual or buccal administration, films/wafers or capsules, suppositories, preparations for the ear or eye, vaginal capsules, aqueous suspensions (lotions, shaking mixtures), lipophilic suspensions, ointments, creams, transdermal therapeutic systems (for example patches), pastes, dusting powders, implants or stents.

The inventive compound may be converted to the application forms listed. This may take place in a known manner by mixing with inert, nontoxic, pharmaceutically suitable excipients. These excipients include carriers (for example, microcrystalline cellulose, lactose, mannitol), solvents (for example, liquid polyethylene glycols), emulsifiers and dispersants or wetting agents (for example, sodium dodecylsulfate, polyoxysorbitan oleate), binders (for example, polyvinylpyrrolidone), synthetic and natural polymers (for example, albumin), stabilizers (for example, antioxidants such as ascorbic acid), dyes (for example, inorganic pigments such as iron oxides) and substances for masking flavors and/or odors.

The present invention further provides medicaments which comprise at least the compound of the formula (I) in the polymorph I, typically together with one or more inert, nontoxic, pharmaceutically suitable excipients, for example binders, fillers, etc, and to the use thereof for the aforementioned purposes.

Dosage of the Pharmaceutical Compositions of the Present Invention:

Based upon standard laboratory techniques known to evaluate compounds useful for the treatment of any of the aforementioned disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered can range from about 0.001 mg/kg to about 200 mg/kg, and preferably from about 0.1 mg/kg to about 50 mg/kg body weight per day. A unit dosage may preferably contain from about 5 mg to about 4000 mg of active ingredient, and can be administered one or more times per day. The daily dosage for oral administration will preferably be from 0.1 to 50 mg/kg of total body weight. The daily dosage for administration by injection, including intravenous, intramuscular, subcutaneous and parenteral injections, and use of infusion techniques will preferably be from 0.1 to 10 mg/kg of total body weight. The daily rectal dosage regimen will preferably be from 0.1 to 50 mg/kg of total body weight. The daily vaginal dosage regimen will preferably be from 0.1 to 50 mg/kg of total body weight. The daily topical dosage regimen will preferably be from 0.1 to 10 mg/kg administered between one to four times daily. The transdermal concentration will preferably be that required to maintain a daily dose of from 0.1 to 10 mg/kg. The daily inhalation dosage regimen will preferably be from 0.1 to 10 mg/kg of total body weight. Other dosages and amounts can be selected routinely.

Nevertheless, it may in some cases be advantageous to deviate from the amounts specified, depending on body weight, administration route, individual behavior toward the active ingredient, type of preparation and time or interval over which the administration is effected. For instance, less than the aforementioned minimum amounts may be sufficient in some cases, while the upper limit specified has to be exceeded in other cases. In the case of administration of relatively large amounts, it may be advisable to divide these into several individual doses over the day.

Process for Preparing:

The invention further provides a process for preparing the compound of the formula (I) in the polymorph I, by effecting the compound of the formula (I) in the polymorph II, obtained as described in example 1, in an inert solvent at a temperature of, for example, from 50° C. up to the reflux temperature of the solvent, preferably from 60 to 80° C., in the absence of crystals of a solvate of the compound of the formula (I), for example in the absence of crystals of the methanol solvate or the ethanol solvate of the compound of formula (I), for up to one day. The mixture is cooled to from −30° C. to room temperature, preferably from −25° C. to 10° C., and the crystals are isolated and dried. The compound of the formula (I) is thus obtained in the polymorph I.

The invention likewise provides a process for preparing the compound of the formula (I) in the polymorph I, by effecting the compound of the formula (I) in the polymorph II, obtained as described in example 1, in an inert solvent at a temperature of, for example, from 10° C. up to the reflux temperature of the solvent, preferably at room temperature, for up to one day. Subsequently, the mixture is seeded with crystals of the compound of the formula (I) in the polymorph I and stirred or shaken, for example at room temperature, for from 1 hour to 14 days, preferably from 2 hours to 7 days. The crystals are isolated and dried. The compound of the formula (I) is thus obtained in the polymorph I.

The invention likewise provides a process for preparing the compound of the formula (I) in the polymorph I, by effecting the compound of the formula (I) in the polymorph II, obtained as described in example 1, in an inert solvent until the desired degree of conversion is attained, preferably until quantitative conversion to the polymorph I. If appropriate, crystals of the compound of the formula (I) in the polymorph I are added. The resulting crystals are isolated and, to remove solvent present, dried to constant weight at room temperature or at elevated temperature, for example from 40 to 80° C. The compound of the formula (I) is thus obtained in the polymorph I.

Effecting the compound of the formula (I) in the polymorph II in an inert solvent means, that for example the compound of the formula (I) in the polymorph II is dissolved completely (solution) or only in part (suspension). The mixture can be, for example stirred or shaken.

Suitable inert solvents are lower alcohols, for example methanol, ethanol, n-propanol, isopropanol, n-butanol, sec-butanol, isobutanol, or ketones such as acetone, or alkanes such as n-pentane, cyclopentane, n-hexane, cyclohexane, or tetrahydrofuran, or acetonitrile, or toluene, or ethyl acetate, or mixtures of the solvents mentioned, or mixtures of the solvents mentioned with water. Preference is given to methanol, ethanol, n-propanol, isopropanol, acetone, tetrahydrofuran, acetonitrile, toluene, ethyl acetate, mixtures of the solvents mentioned or mixtures of the solvents mentioned with water. Isopropanol, ethylacetate or a mixture thereof are used most preferably as inert solvents.

Preference is given to preparing the compound of the formula (I) in the polymorph I by effecting the compound of the formula (I) in the polymorph II, obtained as described in example 1, in methanol, ethanol, a mixture of both solvents or a mixture of both solvents with water, preferably a 1:1 mixture with water, and shaking or stirring at a temperature of from 50° C. up to the reflux temperature of the solvent, preferably at from 60 to 80° C., in the absence of crystals of a solvate of the compound of the formula (I), for example in the absence of crystals of the methanol solvate or the ethanol solvate of the compound of formula (I), for up to one day. The crystals are cooled to from −30° C. to room temperature, preferably from −25 to 10° C., isolated and dried. The compound of the formula (I) is thus obtained in the polymorph I. Most preferably isopropanol, ethylacetate or a mixture thereof is used as solvent.

Preference is likewise given to preparing the compound of the formula (I) in the polymorph I by effecting the compound of the formula (I) in the polymorph II, obtained as described in example 1, in methanol, ethanol, a mixture of both solvents or a mixture of both solvents with water, and shaking or stirring at a temperature of from 10° C. up to the reflux temperature of the solvent, preferably at room temperature, for up to 1 day. The mixture is subsequently seeded with crystals of the compound of the formula (I) in the polymorph I and stirred or shaken, for example at room temperature, for from 1 hour to 14 days, preferably from 2 hours to 7 days. The crystals are isolated and dried. The compound of the formula (I) is thus obtained in the polymorph I. Most preferably isopropanol, ethylacetate or a mixture thereof is used as solvent.

Preference is likewise given to preparing the compound of the formula (I) in the polymorph I by effecting the compound of the formula (I) in the polymorph II, obtained as described in example 1, in an inert solvent apart from methanol and/or ethanol, preferably isopropanol, acetone, tetrahydrofuran, acetonitrile, ethyl acetate, toluene, or a mixture thereof and stirring or shaking at a temperature of from 10° C. up to the reflux temperature of the solvent, preferably at from room temperature to 90° C., for up to 2 weeks, preferably from 1 day up to one week. If appropriate, the mixture is cooled to room temperature and the crystals are isolated and dried. The compound of the formula (I) is thus obtained in the polymorph I. Most preferably isopropanol, ethylacetate or a mixture thereof is used as solvent.

The compound of the formula (I) may likewise be prepared in the polymorph I by heating the compound of the formula (I) in the polymorph II to from 195 to 222° C., preferably from 195 to 215° C., for example at a heating rate of from 10° C. to 30° C. per minute, preferably from 15° C. to 25° C. per minute, and subsequently cooling to from 10° C. to 30° C., preferably to room temperature, for example at a cooling rate of from 1° C. to 4° C. per minute, preferably from 1° C. to 3° C. per minute.

The compound of the formula (I) in the polymorph III can be prepared by effecting the compound of the formula (I) in the polymorph II in an inert solvent, for example methanol. Filtration is effected after from 1 day to 1 week, and the product is dried and heat-treated at from 145 to 160° C. for from 15 minutes to 1 hour. The compound of the formula (I) is thus obtained in the polymorph III.

The methanol solvate of the compound of the formula (I) can be prepared by effecting the compound of the formula (I) in the polymorph II in methanol. After 1 week, filtration is effected, and the product is dried and stored under a methanol atmosphere for from 5 hours to 1 week. The methanol solvate of the compound of the formula (I) is thus obtained with a methanol content of 4.8% by weight.

The ethanol solvate of the compound of the formula (I) can be prepared by effecting the compound of the formula (I) in the polymorph II in ethanol. After 1 week, filtration is effected and the product is dried. The ethanol solvate of the compound of the formula (I) is thus obtained with an ethanol factor of 6.7 percent by weight.

The processes are generally carried out at atmospheric pressure. However, it is also possible to work at elevated pressure or at reduced pressure (for example in a range of from 0.5 to 5 bar).

The weight data in the tests and examples which follow are, unless stated otherwise, percentages by weight; parts are parts by weight. Solvent ratios, dilution ratios and concentration data of liquid/liquid solutions are based on each case on the volume.

WORKING EXAMPLES

The thermograms were obtained using a DSC 7 or Pyris-1 differential scanning calorimeter and TGA 7 thermogravimetric analyzer from Perkin-Elmer. The X-ray diffractograms were registered in a Stoe transmission diffractometer. The IR, FIR, NIR and Raman spectra were recorded using IFS 66v (IR, FIR), IFS 28/N (NIR) and RFS 100 (Raman) Fourier spectrometers from Bruker.

Example 1

4-{4-[({[4-Chloro-3-(trifluoromethyl)phenyl]amino}carbonyl)amino]phenoxy}-N-methylpyridine-2-carboxamide tosylate in the polymorph II 903 g of 4-{4-[({[4-chloro-3-(trifluoromethyl)phenyl]amino}carbonyl)amino]phenoxy}-N-methyl-pyridine-2-carboxamide, prepared as described in WO 00/42012, are initially charged in 2700 ml of ethanol. 451.7 g of p-toluenesulfonic acid monohydrate are dissolved in 1340 g of ethanol and added dropwise at room temperature. The suspension is stirred at room temperature for 1 hour, then filtered off with suction, and the residue is washed three times with 830 ml each time of ethanol. The drying is effected at 50° C. under reduced pressure with supply of air. 1129.6 g of the title compound in the polymorph II are obtained.

Example 2

Preparation of 4-{4-[({[4-chloro-3-(trifluoromethyl)phenyl]amino}carbonyl)-amino]phenoxy}-N-methylpyridine-2-carboxamide tosylate in the polymorph I Example 2.1

5 mg of the tosylate salt of 4-{4-[({[4-chloro-3-(trifluoromethyl)phenyl]amino}carbonyl)amino]-phenoxy}-N-methylpyridine-2-carboxamide in the polymorph II are heated to 200° C. at a heating rate of 20° C./min and subsequently cooled to room temperature at a cooling rate of 2° C./min. The sample is tested thermoanalytically (DSC) and corresponds to the title compound in the polymorph I.

Example 2.2

75 mg of the tosylate salt of 4-{4-[({[4-chloro-3-(trifluoromethyl)phenyl]amino}carbonyl)-amino]phenoxy}-N-methylpyridine-2-carboxamide in polymorph II are dissolved in 10 ml of ethanol/water (1:1) at approximately 80° C. and filtered. The mixture is divided into two samples and sample A is crystallized in a refrigerator at +8° C. and sample B in a freezer at −20° C. After vaporization of the solvent mixtures, the two crystals of sample A and B are tested thermoanalytically (DSC). Both samples correspond to the title compound in the polymorph I.

Example 2.3

In each case 400 mg of the tosylate salt of 4-{4-[({[4-chloro-3-(trifluoromethyl)phenyl]-amino}carbonyl)amino]phenoxy}-N-methylpyridine-2-carboxamide in the polymorph II are suspended in a) 8 ml of methanol and b) in 8 ml of ethanol and each stirred at room temperature for 2 hours. The suspensions are each seeded with 2 mg of the title compound in the polymorph I and subsequently stirred at room temperature for 1 week. After filtration, the solid residues of the two samples are dried at room temperature. The residues are each tested thermoanalytically (DSC) and correspond to the title compound in the polymorph I.

Example 2.4

200 mg of the tosylate salt of 4-{4-[({[4-chloro-3-(trifluoromethyl)phenyl]amino}carbonyl)-amino]phenoxy}-N-methylpyridine-2-carboxamide in the polymorph II are suspended in 5 ml of ethanol/water (1:1 v/v) and stirred at room temperature for 2 hours. The suspension is seeded with 2 mg of the title compound in the polymorph I and subsequently stirred at room temperature for 1 week. After filtration, the solid residue is dried at room temperature. The residue is tested thermoanalytically (DSC) and corresponds to the title compound in the polymorph I.

Example 2.5

In each case 50 mg of the tosylate salt of 4-{4-[({[4-chloro-3-(trifluoromethyl)phenyl]amino}-carbonyl)amino]phenoxy}-N-methylpyridine-2-carboxamide in the polymorph II are admixed with in each case 2 ml of a) isopropanol, b) acetone, c) tetrahydrofuran, d) acetonitrile, e) ethyl acetate and f) toluene, and in each case stirred at room temperature for 6 days. In the case of c) tetrahydrofuran and f) toluene another 1 ml of the particular solvent is added. The suspensions are each filtered and the particular residues are dried at room temperature. The residues are each tested by X-ray diffractometry and correspond to the title compound in the polymorph I.

Example 2.6

200 mg of the tosylate salt of 4-{4-[({[4-chloro-3-(trifluoromethyl)phenyl]amino}carbonyl)-amino]phenoxy}-N-methylpyridine-2-carboxamide in the polymorph II are suspended in 4 ml of toluene and the suspension is stirred at 80° C. for one week. After cooling to room temperature, the residue is filtered, dried at room temperature and tested by X-ray diffractometry. The title compound is obtained in the polymorph I.

Example 3

Preparation of 4-{4-[({[4-chloro-3-(trifluoromethyl)phenyl]amino}carbonyl)-amino]phenoxy}-N-methylpyridine-2-carboxamide tosylate in the polymorph III 3.5 g of the tosylate salt of 4-{4-[({[4-chloro-3-(trifluoromethyl)phenyl]amino}carbonyl)-amino]phenoxy}-N-methylpyridine-2-carboxamide in the polymorph II are suspended in 15 ml of methanol and stirred at room temperature. After one week, the suspension is filtered and the residue dried at room temperature. Subsequently, the product is heat-treated at 150° C. for 30 min. The residue is analyzed by X-ray diffractometry and corresponds to the title compound in the polymorph III.

Example 4

Preparation of the methanol solvate of 4-{4-[({[4-chloro-3-(trifluoromethyl)phenyl]amino}carbonyl)amino]phenoxy}-N-methylpyridine-2-carboxamide tosylate 3.5 g of the tosylate salt of 4-{4-[({[4-chloro-3-(trifluoromethyl)phenyl]amino}carbonyl)amino]-phenoxy}-N-methylpyridine-2-carboxamide in the polymorph II are suspended in 15 ml of methanol and stirred at room temperature. After one week, the suspension is filtered and the residue is dried at room temperature. Subsequently, the product is stored in a desiccator with a methanol atmosphere for one day. The residue is analyzed by X-ray diffractometry and corresponds to the methanol solvate of the title compound with a methanol content of 4.8 percent by weight.

Example 5

Preparation of the ethanol solvate of 4-{4-[({[4-chloro-3-(trifluoromethyl)phenyl]amino}carbonyl)amino]phenoxy}-N-methylpyridine-2-carboxamide tosylate 3 g of the tosylate salt of 4-{4-[({[4-chloro-3-(trifluoromethyl)phenyl]amino}carbonyl)amino]-phenoxy}-N-methylpyridine-2-carboxamide in the polymorph II are suspended in 15 ml of ethanol and stirred at room temperature. After one week, the suspension is filtered and the residue is dried at room temperature. The residue is analyzed by X-ray diffractometry and corresponds to the ethanol solvate of the title compound with an ethanol content of 6.7 percent by weight.

TABLE 1

Differential Scanning Calorimetry and Thermogravimetry

| | Polymorph I | Polymorph II | Polymorph III | Methanol-solvate | Ethanol solvate |
|---|---|---|---|---|---|
| Melting point [° C.] | 223-231* | 194** | 187-190 | — | — |
| Loss in mass [% by wt.] | <0.5 | <0.5 | <0.5 | 4.8 | 6.7 |

*= melting under decomposition
**= Conversion point

TABLE 2

X-ray diffractometry Reflections

| Polymorph I [2 theta] | Polymorph II [2 theta] | Polymorph III [2 theta] | Methanol solvate [2 theta] | Ethanol solvate [2 theta] |
|---|---|---|---|---|
| 4.4 | 7.3 | 7.7 | 8.0 | 7.9 |
| 10.7 | 8.8 | 8.5 | 8.4 | 8.4 |
| 11.1 | 10.5 | 9.8 | 9.3 | 9.3 |
| 11.4 | 12.4 | 10.6 | 11.2 | 9.5 |
| 11.6 | 12.8 | 12.0 | 12.2 | 11.2 |
| 12.2 | 13.1 | 12.3 | 13.0 | 12.0 |
| 12.8 | 13.4 | 12.9 | 13.4 | 12.2 |
| 13.2 | 13.6 | 13.4 | 15.8 | 12.8 |
| 14.8 | 14.0 | 13.5 | 16.3 | 13.4 |
| 16.5 | 14.7 | 15.4 | 16.9 | 15.9 |
| 16.7 | 15.5 | 16.0 | 17.7 | 16.1 |
| 17.7 | 15.7 | 16.5 | 18.3 | 16.8 |
| 17.9 | 15.9 | 16.9 | 18.7 | 17.4 |
| 18.8 | 16.4 | 17.3 | 19.0 | 17.7 |
| 19.3 | 17.0 | 17.8 | 19.4 | 18.1 |
| 19.6 | 17.6 | 18.7 | 20.2 | 18.3 |
| 20.1 | 17.9 | 18.8 | 20.5 | 18.6 |
| 20.5 | 18.3 | 19.3 | 20.9 | 18.8 |
| 20.8 | 19.3 | 19.9 | 21.4 | 19.4 |
| 21.5 | 20.2 | 20.3 | 21.7 | 20.0 |
| 21.7 | 20.8 | 20.8 | 22.3 | 20.4 |
| 22.3 | 21.1 | 21.2 | 22.4 | 21.0 |
| 22.5 | 21.9 | 21.6 | 23.8 | 21.2 |
| 22.9 | 22.6 | 22.5 | 24.0 | 21.5 |
| 23.4 | 22.8 | 23.0 | 24.4 | 21.7 |
| 23.7 | 23.2 | 23.4 | 24.7 | 22.3 |
| 24.0 | 24.0 | 24.2 | 24.9 | 22.4 |
| 24.5 | 24.6 | 24.5 | 25.2 | 22.8 |
| 25.1 | 25.4 | 24.8 | 25.7 | 23.3 |
| 25.4 | 25.9 | 25.2 | 26.0 | 23.6 |
| 26.0 | 26.7 | 25.9 | 26.1 | 23.8 |
| 26.4 | 27.1 | 26.9 | 26.4 | 24.3 |
| 26.6 | 28.2 | 27.5 | 26.9 | 24.7 |
| 27.0 | 28.4 | 27.7 | 27.0 | 25.3 |
| 27.6 | 29.7 | 28.2 | 27.5 | 25.8 |
| 28.2 | 30.7 | 29.2 | 27.7 | 25.9 |
| 28.6 | 31.4 | 29.4 | 28.1 | 26.4 |
| 28.8 | 32.5 | 29.8 | 28.3 | 26.9 |
| 29.3 | 33.4 | 30.3 | 28.8 | 27.3 |
| 29.6 | 34.7 | 31.4 | 29.1 | 27.6 |
| 29.9 | 35.0 | 32.2 | 29.7 | 28.3 |
| 30.8 | 35.9 | 33.5 | 30.2 | 28.8 |
| 31.2 | 36.5 | 34.0 | 30.4 | 29.1 |
| 31.6 | | 35.2 | 30.7 | 29.5 |
| 31.8 | | 36.1 | 30.8 | 29.7 |
| 32.1 | | 37.2 | 31.4 | 30.2 |
| 32.4 | | 37.7 | 31.6 | 30.4 |
| 32.7 | | | 31.9 | 30.9 |
| 33.1 | | | 32.3 | 31.4 |
| 33.8 | | | 32.6 | 32.0 |
| 34.2 | | | 32.9 | 32.6 |
| 34.6 | | | 33.4 | 32.9 |
| 35.4 | | | 33.8 | 33.2 |
| 35.7 | | | 34.0 | 33.7 |
| 37.1 | | | 34.2 | 33.9 |
| | | | 34.5 | 34.5 |

TABLE 2-continued

X-ray diffractometry Reflections

| Polymorph I [2 theta] | Polymorph II [2 theta] | Polymorph III [2 theta] | Methanol solvate [2 theta] | Ethanol solvate [2 theta] |
|---|---|---|---|---|
|  |  |  | 34.9 | 35.5 |
|  |  |  | 36.2 | 36.0 |
|  |  |  | 36.6 | 36.3 |
|  |  |  | 37.2 | 36.6 |
|  |  |  | 37.7 | 37.1 |
|  |  |  |  | 37.7 |

TABLE 3

IR spectroscopy Peak maxima

| Polymorph I [$cm^{-1}$] | Polymorph II [$cm^{-1}$] | Polymorph III [$cm^{-1}$] | Methanol solvate [$cm^{-1}$] | Ethanol solvate [$cm^{-1}$] |
|---|---|---|---|---|
| 3390 | 3345 | 3374 | 3317 | 3313 |
| 3289 | 3277 | 3280 | 3098 | 3237 |
| 3256 | 3108 | 3250 | 3072 | 3067 |
| 3212 | 3073 | 3081 | 2948 | 2980 |
| 3144 | 2944 | 2955 | 2836 | 2895 |
| 3113 | 1908 | 1917 | 1712 | 1710 |
| 3080 | 1718 | 1715 | 1692 | 1692 |
| 2943 | 1696 | 1691 | 1632 | 1633 |
| 1908 | 1632 | 1632 | 1608 | 1607 |
| 1724 | 1597 | 1604 | 1546 | 1545 |
| 1689 | 1547 | 1551 | 1506 | 1505 |
| 1630 | 1521 | 1539 | 1483 | 1483 |
| 1611 | 1506 | 1526 | 1464 | 1465 |
| 1598 | 1486 | 1503 | 1406 | 1406 |
| 1558 | 1468 | 1484 | 1337 | 1337 |
| 1529 | 1403 | 1461 | 1314 | 1314 |
| 1506 | 1333 | 1418 | 1287 | 1286 |
| 1485 | 1307 | 1404 | 1258 | 1258 |
| 1458 | 1287 | 1385 | 1232 | 1234 |
| 1419 | 1255 | 1337 | 1193 | 1191 |
| 1401 | 1237 | 1308 | 1170 | 1171 |
| 1327 | 1206 | 1284 | 1140 | 1140 |
| 1310 | 1189 | 1258 | 1128 | 1115 |
| 1281 | 1163 | 1234 | 1115 | 1044 |
| 1256 | 1135 | 1209 | 1030 | 1035 |
| 1239 | 1125 | 1189 | 1017 | 1005 |
| 1220 | 1116 | 1178 | 1008 | 947 |
| 1189 | 1031 | 1140 | 947 | 925 |
| 1182 | 1007 | 1127 | 925 | 896 |
| 1132 | 944 | 1118 | 904 | 879 |
| 1117 | 920 | 1034 | 877 | 861 |
| 1032 | 900 | 1010 | 848 | 849 |
| 1009 | 880 | 947 | 831 | 830 |
| 950 | 843 | 920 | 822 | 823 |
| 939 | 827 | 900 | 779 | 778 |
| 922 | 813 | 877 | 744 | 744 |
| 879 | 787 | 842 | 720 | 721 |
| 846 | 779 | 834 | 711 | 711 |
| 822 | 745 | 825 | 683 | 682 |
| 777 | 720 | 818 | 663 | 663 |
| 748 | 709 | 776 | 617 | 592 |
| 721 | 684 | 744 | 591 | 570 |
| 711 | 660 | 721 | 571 | 562 |
| 681 | 568 | 710 | 561 | 533 |
| 662 | 552 | 683 | 534 | 510 |
| 565 | 544 | 663 | 509 |  |
| 553 | 505 | 572 | 488 |  |
| 533 |  | 564 | 468 |  |
| 513 |  | 548 | 442 |  |
|  |  | 509 |  |  |
|  |  | 484 |  |  |
|  |  | 469 |  |  |
|  |  | 443 |  |  |

TABLE 4

Raman spectroscopy Peak maxima

| Polymorph I [$cm^{-1}$] | Polymorph II [$cm^{-1}$] | Polymorph III [$cm^{-1}$] | Methanol solvate [$cm^{-1}$] | Ethanol solvate [$cm^{-1}$] |
|---|---|---|---|---|
| 3113 | 3115 | 3107 | 3098 | 3094 |
| 3100 | 3095 | 3069 | 3066 | 3066 |
| 3068 | 3064 | 3016 | 2929 | 3046 |
| 2986 | 3052 | 2958 | 2838 | 2977 |
| 2951 | 2924 | 2930 | 1711 | 2927 |
| 2925 | 2812 | 2883 | 1688 | 2884 |
| 2817 | 1719 | 2814 | 1608 | 2812 |
| 2577 | 1696 | 2741 | 1548 | 1710 |
| 1723 | 1609 | 1715 | 1507 | 1690 |
| 1689 | 1604 | 1690 | 1406 | 1635 |
| 1613 | 1550 | 1632 | 1386 | 1607 |
| 1606 | 1521 | 1605 | 1334 | 1547 |
| 1556 | 1507 | 1567 | 1313 | 1506 |
| 1529 | 1414 | 1549 | 1299 | 1461 |
| 1506 | 1402 | 1504 | 1266 | 1406 |
| 1442 | 1376 | 1475 | 1235 | 1385 |
| 1419 | 1334 | 1448 | 1213 | 1334 |
| 1401 | 1312 | 1413 | 1193 | 1313 |
| 1369 | 1268 | 1404 | 1172 | 1299 |
| 1328 | 1255 | 1386 | 1114 | 1288 |
| 1310 | 1234 | 1334 | 1033 | 1264 |
| 1278 | 1207 | 1310 | 1004 | 1235 |
| 1267 | 1161 | 1284 | 925 | 1213 |
| 1245 | 1136 | 1265 | 863 | 1194 |
| 1212 | 1116 | 1236 | 819 | 1168 |
| 1186 | 1103 | 1215 | 802 | 1141 |
| 1163 | 1031 | 1180 | 786 | 1113 |
| 1134 | 1009 | 1161 | 746 | 1033 |
| 1117 | 944 | 1120 | 721 | 1017 |
| 1032 | 922 | 1106 | 684 | 1003 |
| 1010 | 858 | 1034 | 663 | 925 |
| 922 | 825 | 1009 | 638 | 891 |
| 880 | 813 | 926 | 618 | 862 |
| 862 | 798 | 860 | 555 | 850 |
| 824 | 787 | 815 | 492 | 819 |
| 802 | 746 | 801 | 442 | 802 |
| 789 | 718 | 785 | 397 | 786 |
| 749 | 684 | 746 | 372 | 779 |
| 722 | 662 | 716 | 359 | 746 |
| 692 | 636 | 683 | 339 | 720 |
| 683 | 568 | 663 | 310 | 694 |
| 663 | 553 | 637 | 297 | 684 |
| 637 |  | 619 | 235 | 663 |
| 552 |  | 553 | 176 | 638 |
| 492 |  | 510 | 130 | 616 |
| 471 |  | 461 | 109 | 590 |
| 445 |  | 443 |  | 553 |
| 436 |  | 418 |  | 512 |
| 423 |  |  |  | 491 |
| 399 |  |  |  | 459 |
| 390 |  |  |  | 442 |
| 367 |  |  |  | 396 |
| 313 |  |  |  | 387 |
| 305 |  |  |  | 373 |
| 292 |  |  |  | 362 |
| 231 |  |  |  | 353 |
|  |  |  |  | 337 |
|  |  |  |  | 313 |
|  |  |  |  | 306 |
|  |  |  |  | 295 |
|  |  |  |  | 237 |
|  |  |  |  | 217 |
|  |  |  |  | 181 |
|  |  |  |  | 109 |

TABLE 5

FIR spectroscopy Peak maxima

| Polymorph I [cm⁻¹] | Polymorph II [cm⁻¹] | Polymorph III [cm⁻¹] | Methanol solvate [cm⁻¹] | Ethanol solvate [cm⁻¹] |
|---|---|---|---|---|
| 495 | 496 | 484 | 489 | 490 |
| 470 | 468 | 468 | 468 | 469 |
| 458 | 457 | 443 | 460 | 459 |
| 445 | 443 | 432 | 442 | 441 |
| 436 | 429 | 423 | 433 | 433 |
| 423 | 413 | 417 | 425 | 426 |
| 408 | 400 | 396 | 397 | 396 |
| 399 | 386 | 381 | 386 | 387 |
| 368 | 366 | 370 | 372 | 373 |
| 356 | 345 | 358 | 358 | 353 |
| 321 | 321 | 351 | 351 | 337 |
| 304 | 304 | 335 | 338 | 318 |
| 291 | 293 | 309 | 316 | 294 |
| 252 | 255 | 301 | 296 | 280 |
| 238 | 237 | 290 | 280 | 266 |
| 210 | 213 | 255 | 252 | 252 |
| 173 | 190 | 241 | 236 | 237 |
| 120 | 175 | 224 | 216 | 216 |
| 114 | 156 | 210 | 178 | 180 |
|  | 137 | 177 | 146 | 166 |
|  | 106 | 147 | 114 | 152 |
|  |  | 108 | 104 | 143 |
|  |  |  | 99 | 116 |
|  |  |  |  | 106 |
|  |  |  |  | 97 |
|  |  |  |  | 93 |

TABLE 6

NIR spectroscopy Peak maxima

| Polymorph I [cm⁻¹] | Polymorph II [cm⁻¹] | Polymorph III [cm⁻¹] | Methanol solvate [cm⁻¹] | Ethanol solvate [cm⁻¹] |
|---|---|---|---|---|
| 8820 | 8791 | 8843 | 8829 | 8828 |
| 8407 | 8395 | 8420 | 8424 | 8442 |
| 8186 | 8167 | 8200 | 7191 | 7191 |
| 7182 | 7122 | 7155 | 6421 | 6631 |
| 6934 | 6111 | 6658 | 6081 | 6422 |
| 6664 | 6017 | 6510 | 6024 | 6073 |
| 6494 | 5974 | 6432 | 5964 | 6022 |
| 6087 | 5914 | 6108 | 5896 | 5962 |
| 6030 | 5789 | 6023 | 5555 | 5891 |
| 5988 | 5746 | 5891 | 5288 | 5785 |
| 5934 | 5641 | 5793 | 4908 | 5287 |
| 5881 | 5555 | 5739 | 4661 | 4908 |
| 5747 | 5501 | 5652 | 4606 | 4659 |
| 5648 | 5339 | 5262 | 4574 | 4605 |
| 5338 | 5219 | 4982 | 4404 | 4572 |
| 4984 | 4895 | 4919 | 4329 | 4421 |
| 4914 | 4789 | 4847 | 4278 | 4346 |
| 4791 | 4661 | 4788 | 4207 | 4259 |
| 4691 | 4606 | 4708 | 4174 | 4202 |
| 4573 | 4563 | 4666 | 4080 | 4170 |
| 4399 | 4512 | 4571 | 4057 | 4096 |
| 4312 | 4403 | 4409 |  | 4080 |
| 4275 | 4275 | 4344 |  | 4051 |
| 4208 | 4226 | 4305 |  |  |
| 4088 | 4155 | 4282 |  |  |
|  | 4095 | 4227 |  |  |
|  | 4064 | 4200 |  |  |
|  |  | 4091 |  |  |
|  |  | 4063 |  |  |

What is claimed is:

1. A compound of the formula (I)

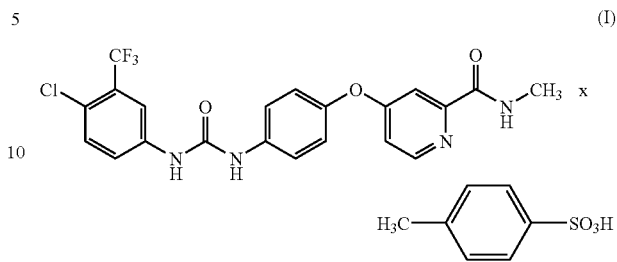

in the polymorph I form, which shows in the X-ray diffractometry peak maxima of the 2 theta angle of 4.4, 14.8 and 20.5.

2. The compound of claim 1 which shows in the X-ray diffractometry peak maxima of the 2 theta angle comprising 4.4, 14.8, 20.5, 20.8, 21.5 and 22.9.

3. The compound of claim 1 which shows in the IR spectrum a peak maximum of 1724 cm⁻¹.

4. The compound of claim 1 which shows in the Raman spectrum a peak maximum of 1723 cm⁻¹.

5. A method of preparing the compound of formula (I)

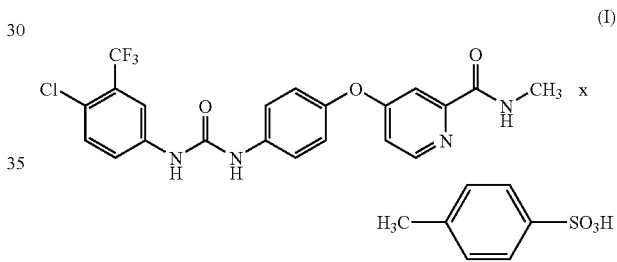

in the polymorph I form which shows in the X-ray diffractometry peak maxima of the 2 theta angle of 4.4, 14.8 and 20.5, comprising contacting a compound of formula (I) in the polymorph II form with an inert solvent under conditions sufficient to quantitatively convert the compound in the polymorph II form to the polymorph I form.

6. The method according to claim 5, further comprising the step of seeding the inert solvent with crystals of a compound of the formula (I) in the polymorph I form.

7. A method of preparing a compound of formula (I)

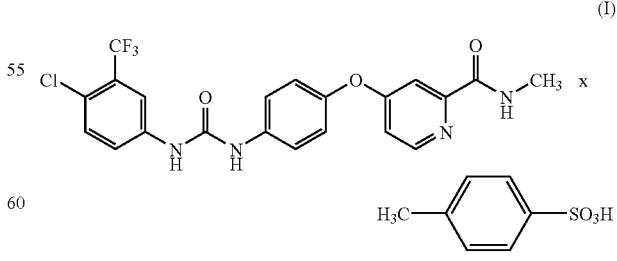

in the polymorph I form which shows in the X-ray diffractometry peak maxima of the 2 theta angle of 4.4, 14.8 and 20.5, comprising heating a compound of formula (I) in the polymorph II form from 195° C. to 222° C. at a heating rate of 10° C. to 30° C. per minute and subsequently cooling to 10° C. to 30° C. at a cooling rate of from 1 to 4° C. per minute.

8. A pharmaceutical composition comprising a compound of formula (I):

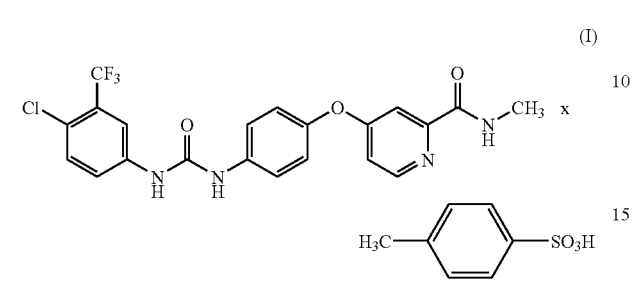

substantially in the polymorph I form which shows in the X-ray diffractometry peak maxima of the 2 theta angle of 4.4, 14.8 and 20.5.

9. The pharmaceutical composition as claimed in claim 8, further comprising one or more inert, nontoxic, pharmaceutically suitable excipients.

10. The pharmaceutical composition of claim 8, wherein the compound of formula (I) is present in the polymorph I form in the composition in an amount equal to or more than 90 percent by weight of the total weight of the compound of formula (I) present in the composition.

11. The pharmaceutical composition according to claim 8, further comprising another pharmaceutical agent where the combination causes no unacceptable side effects.

12. The pharmaceutical composition of claim 8, further comprising another pharmaceutical agent which is a cytotoxic agent, a signal transduction inhibitor, an anti-cancer agent, or an antiemetic.

13. A pharmaceutical composition comprising a compound of formula (I):

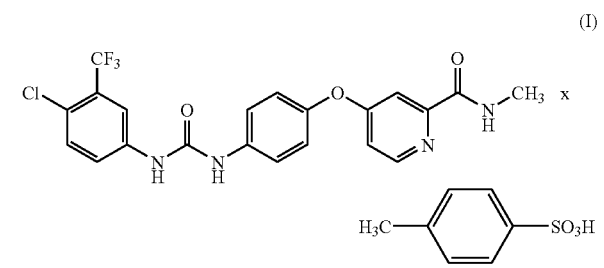

substantially in the polymorph I form which shows in the X-ray diffractometry peak maxima of the 2 theta angle of 4.4, 14.8 and 20.5, and at least one additional pharmaceutical agent.

14. The pharmaceutical composition of claim 13, further comprising one or more inert, nontoxic, pharmaceutically suitable excipients.

15. The pharmaceutical composition of claim 13, wherein said additional pharmaceutical agent is a cytotoxic agent, a signal transduction inhibitor, an anti-cancer agent, or an antiemetic.

16. A method of treating a disorder, comprising administering to a subject in need thereof a therapeutically effective amount of a compound of formula (I)

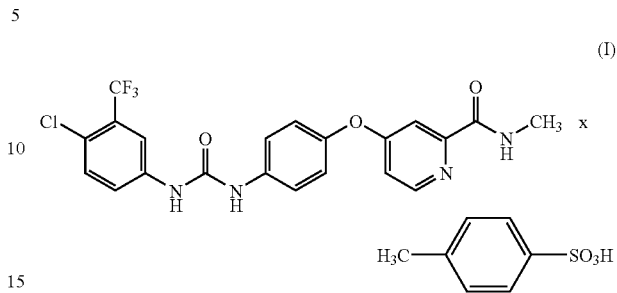

in the polymorph I form which shows in the X-ray diffractometry peak maxima of the 2 theta angle of 4.4, 14.8 and 20.5.

17. The method of claim 16, wherein the disorder is selected from the group consisting of abnormal angiogenesis, hyperpermeability processes, bone marrow diseases, carcinoma and carcinogenic cell growth.

18. The method of claim 16, wherein the disorder is leukemia, or carcinoma of the lung, pancreas, thyroid gland, kidney or intestine.

19. A method for treating a disorder, comprising administering to a subject in need thereof a therapeutically effective amount of the pharmaceutical composition of any one of claims 8 to 15.

20. The method of claim 19, wherein the disorder is selected from the group consisting of abnormal angiogenesis, hyperpermeability processes, bone marrow diseases, carcinoma and carcinogenic cell growth.

21. The method of claim 19, wherein the disorder is leukemia, or carcinoma of the lung, pancreas, thyroid gland, kidney or intestine.

22. A method of preparing a compound of formula (I)

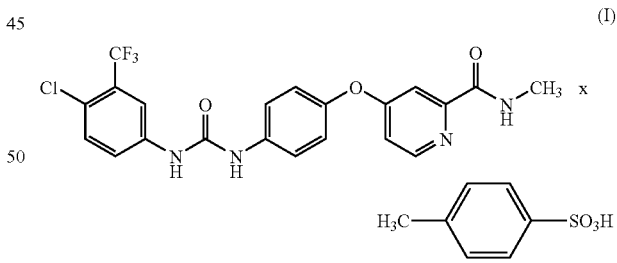

in the polymorph I form which shows in the X-ray diffractometry peak maxima of the 2 theta angle of 4.4, 14.8 and 20.5, comprising dissolving or suspending a compound of formula (I) in the polymorph II form in an inert solvent and stirring or shaking under conditions sufficient to quantitatively convert the compound in the polymorph II form to the polymorph I form.

23. The compound of the formula (I) as claimed in claim 22, wherein the process for its preparation further comprises the step of seeding the inert solvent with crystals of a compound of the formula (I) in the polymorph I form.

24. The compound of claim 1 prepared by dissolving or suspending a compound of formula (I) in the polymorph II form in an inert solvent and stiffing or shaking under conditions sufficient to quantitatively convert the compound in the polymorph II form to the polymorph I form.

25. The compound of claim 1 prepared by dissolving or suspending a compound of formula (I) in the polymorph II form in an inert solvent, seeding the inert solvent with crystals of a compound of the formula (I) in the polymorph I form and stiffing or shaking under conditions sufficient to quantitatively convert the compound in the polymorph II form to the polymorph I form.

26. The compound of claim 1 prepared by a method comprising heating a compound of formula (I) in the polymorph II form from 195° C. to 222° C. at a heating rate of 10° C. to 30° C. per minute and subsequently cooling to 10° C. to 30° C. at a cooling rate of from 1 to 4° C. per minute to quantitatively convert the compound in the polymorph II form to the polymorph I form.

27. The compound of claim 1 which shows in the X-ray diffractometry peak maxima of the 2 theta angle of 4.4, 14.8 and 20.5, which shows in the IR spectrum a peak maximum of 1724 cm$^{-1}$ and which shows in the Raman spectrum a peak maximum of 1723 cm$^{-1}$.

28. A compound having the x-ray diffraction pattern of polymorph I in FIG. 2 of the application which shows in the X-ray diffractometry peak maxima of the 2 theta angle of 4.4, 14.8 and 20.5.

29. The compound of claim 1 which shows in the X-ray diffractometry peak maxima of the 2 theta angle comprising: 4.4, 13.2, 14.8, 16.7, 17.9, 20.1, 20.5, 20.8, 21.5 and 22.9.

30. The compound of claim 1 which shows in the X-ray diffractometry peak maxima of the 2 theta angle comprising: 4.4, 10.7, 11.1, 11.4, 11.6, 12.2, 12.8, 13.2, 14.8, 16.5, 16.7, 17.7, 17.9, 18.8, 19.3, 19.6, 20.1, 20.5, 20.8, 21.5, 21.7, 22.3, 22.5, 22.9, 23.4, 23.7, 24.0, 24.5, 25.1, 25.4, 26.0, 26.4, 26.6, 27.0, 27.6, 28.2, 28.6, 28.8, 29.3, 29.6, 29.9, 30.8, 31.2, 31.6, 31.8, 32.1, 32.4, 32.7, 33.1, 33.8, 34.2, 34.6, 35.4, 35.7 and 37.1.

31. The compound of claim 1 which melts under decomposition at 223° C.-231° C.

* * * * *

UNITED STATES PATENT AND TRADEMARK OFFICE
CERTIFICATE OF CORRECTION

PATENT NO. : 8,877,933 B2  
APPLICATION NO. : 11/664363  
DATED : November 4, 2014  
INVENTOR(S) : Alfons Grunenberg et al.

It is certified that error appears in the above-identified patent and that said Letters Patent is hereby corrected as shown below:

IN THE CLAIMS

Column 23, line 3, claim 24, replace "stiffing" with --stirring--.

Column 23, line 10, claim 25, replace "stiffing" with --stirring--.

Signed and Sealed this  
Fourteenth Day of April, 2015

Michelle K. Lee  
*Director of the United States Patent and Trademark Office*